United States Patent
Cardinali et al.

(10) Patent No.: US 11,407,716 B2
(45) Date of Patent: Aug. 9, 2022

(54) ACRIDINE COMPOUND FOR USE IN AN ELECTRONIC DEVICE AND DISPLAY DEVICE

(71) Applicant: Novaled GmbH, Dresden (DE)

(72) Inventors: Francois Cardinali, Dresden (DE); Benjamin Schulze, Dresden (DE); Jerome Ganier, Dresden (DE); Domagoj Pavicic, Dresden (DE); Volodymyr Senkovskyy, Dresden (DE)

(73) Assignee: Novaled GmbH, Dresden (DE)

( * ) Notice: Subject to any disclaimer, the term of this patent is extended or adjusted under 35 U.S.C. 154(b) by 365 days.

(21) Appl. No.: 16/490,163

(22) PCT Filed: Mar. 2, 2018

(86) PCT No.: PCT/EP2018/055198
§ 371 (c)(1),
(2) Date: Aug. 30, 2019

(87) PCT Pub. No.: WO2018/158438
PCT Pub. Date: Sep. 7, 2018

(65) Prior Publication Data
US 2020/0071276 A1    Mar. 5, 2020

(30) Foreign Application Priority Data
Mar. 2, 2017  (EP) .................................... 17159001

(51) Int. Cl.
*H01L 51/50*  (2006.01)
*C07D 219/02*  (2006.01)
*H01L 51/00*  (2006.01)
*H01L 51/52*  (2006.01)

(52) U.S. Cl.
CPC ........ *C07D 219/02* (2013.01); *H01L 51/0056* (2013.01); *H01L 51/0072* (2013.01);
(Continued)

(58) Field of Classification Search
None
See application file for complete search history.

(56) References Cited

U.S. PATENT DOCUMENTS

2004/0253389 A1* 12/2004 Suzuki ................. C07C 217/92
252/299.01

FOREIGN PATENT DOCUMENTS

EP    2395571 A1    6/2010
EP    2312663 A1    4/2011
(Continued)

OTHER PUBLICATIONS

PCT International Search Report and Written Opinion for PCT Application No. PCT/EP2018/055198 dated Jun. 11, 2018 (9 pages).

*Primary Examiner* — Gregory D Clark
(74) *Attorney, Agent, or Firm* — Eversheds Sutherland (US) LLP

(57) ABSTRACT

The present invention relates to acridine compound of formula structure (I), and to an electron transport layer, which comprises at least one compound of formula (I), an semiconductor layer comprising at least one compound of formula (I) as well as to an electronic device comprising a semiconductor layer thereof.

(Continued)

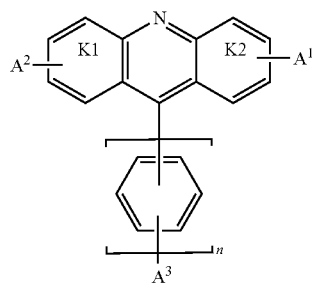

20 Claims, 2 Drawing Sheets

(52) U.S. Cl.
CPC ...... *H01L 51/5012* (2013.01); *H01L 51/5072* (2013.01); *H01L 51/5206* (2013.01); *H01L 51/5221* (2013.01)

(56) References Cited

FOREIGN PATENT DOCUMENTS

| KR | 20150064442 | * | 6/2015 | ............. C09K 11/06 |
| KR | 20150121394 | A | 10/2015 | |
| WO | 2013/079217 | A1 | 6/2013 | |
| WO | 2015/083948 | A1 | 6/2015 | |

* cited by examiner

ACRIDINE COMPOUND FOR USE IN AN ELECTRONIC DEVICE AND DISPLAY DEVICE

CROSS REFERENCE TO RELATED APPLICATIONS

This application is a U.S. national stage application of PCT/EP2018/055198, filed Mar. 2, 2018, which claims priority to European Application No. 17159001.1, filed Mar. 2, 2017. The content of these applications is incorporated herein by reference.

TECHNICAL FIELD

The present invention relates to new acridine compounds and their use as semiconductor material. The present invention relates further to an electronic device comprising the acridine compounds, a device comprising an organic light-emitting diode comprising the acridine compound, a display device thereof and a method of manufacturing the same.

BACKGROUND ART

Organic light-emitting diodes OLEDs, which are self-emitting devices, have a wide viewing angle, excellent contrast, quick response, high brightness, excellent driving voltage characteristics, and color reproduction. A typical OLED includes an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the semiconductor device, and among them, may be affected by characteristics of an organic material of the semiconductor device.

Particularly, development for an organic material being capable of increasing electron mobility and simultaneously increasing electrochemical stability is needed so that the organic light emitting diode may be applied to a large-size flat panel display.

WO2011154131A1 relates to an electronic device comprising at least one organic semiconducting material according to the following formula A): wherein R1-4 are independently selected from H, halogen, CN, substituted or unsubstituted C1-C20-alkyl or heteroalkyl, C6-C20-aryl or C5-C20-heteroaryl, C1-C20-alkoxy or C6-C20-aryloxy, Ar is selected from substituted or unsubstituted C6-C20-aryl or C5-C20-heteroaryl, and R5 is selected from substituted or unsubstituted C6-C20-aryl or C5-C20-heteroaryl, H, F or formula B).

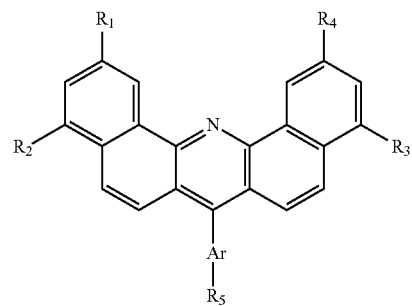

A)

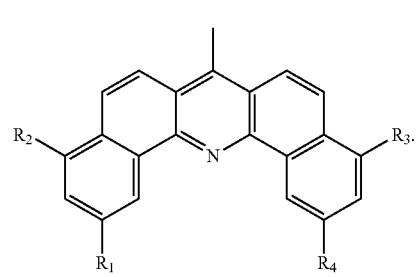

B)

The glass transition temperature is lower, the operating voltage is higher, and cd/A efficiency and lifetime are lower for OLEDs comprising these materials.

In the light of the prior art, there remains a need to improve performance of OLEDs and semiconductor devices, in particular to achieve a higher efficiency and/or longer lifetime through improving the characteristics of the compounds comprised therein.

DISCLOSURE

An aspect of the present invention provides an acridine compound of formula structure I, with a ring system K1 and K2:

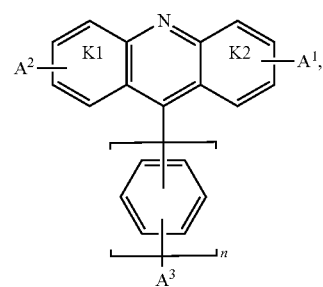

I wherein
n is 0, 1 or 2;
$A^1$ and $A^2$ are independently selected from H or aromatic cyclic ring of unsubstituted or substituted phenylene and the substituents are selected from H, $C_1$ to $C_{18}$ alkyl and $C_1$ to $C_{18}$ alkoxy, and at least one aromatic cyclic ring of $A^1$ and/or $A^2$ are annelated with the ring system K2 or the ring system K1;
$A^3$ has the formulae Ia, having a ring system L1, or
has the formula Ib, having a ring system L2, or
has the formula Ic, or
has the formula Id, or
has the formula Ie, or has the formula If:

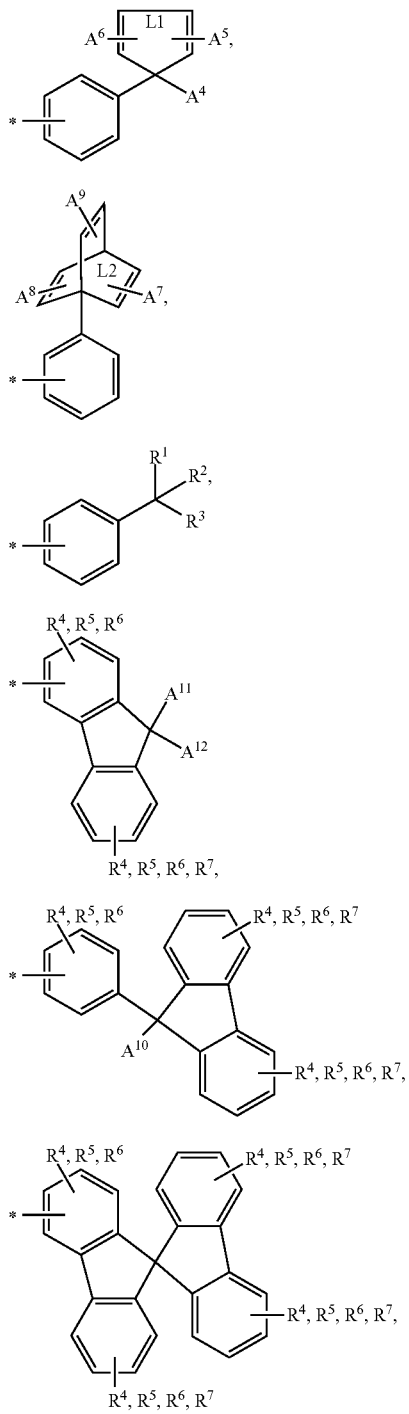

R[1], R[2] are independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy;

R[3] is selected from unsubstituted or substituted $C_6$ to $C_{24}$ aryl, and the substituents are independently selected from H, $C_1$ to $C_{18}$ alkyl and $C_1$ to $C_{18}$ alkoxy;

R[4], R[5], R[6] and R[7] are independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

A[4] to A[12] are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

wherein at least one of A[5] and/or A[6] are annelated with the ring system L1;

wherein at least one of A[7] and/or A[8] and/or A[9] annelated with the ring system L2; and wherein formulas Ia to If of A[3] are connected at the position marked with "*" via a single bond.

According to one embodiment an acridine compound of formula I, with a ring system K1 and K2 is provided:

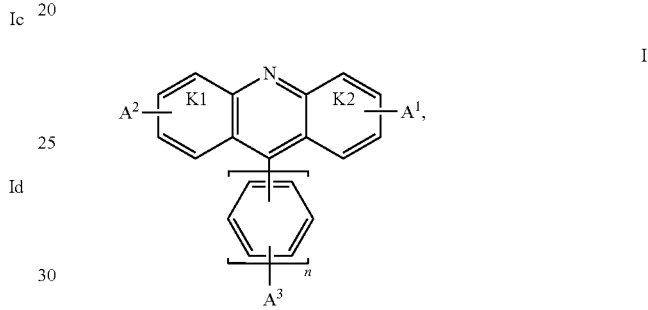

wherein n is 0, 1 or 2;

A[1] and A[2] are independently selected from H or aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of A[1] and/or A[2] are annelated with the ring system K2 or the ring system K1;

A[3] has the formulae Ia, having a ring system L1, or has the formula Ib, having a ring system L2, or has the formula Ic, or has the formula Id, or has the formula Ie, or has the formula If:

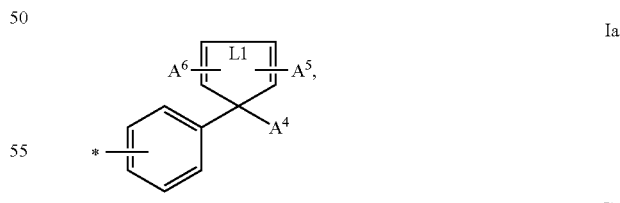

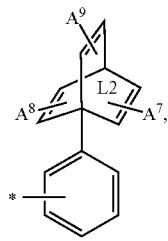

-continued

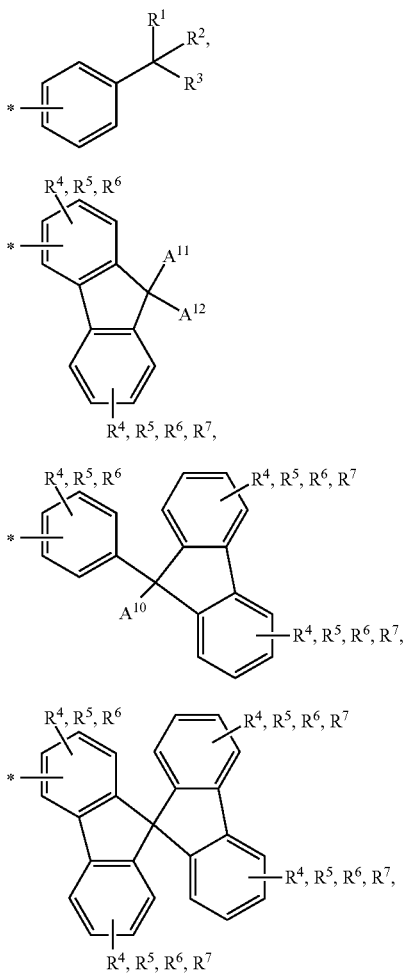

R[1], R[2] are independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy;
R[3] is selected from unsubstituted or substituted $C_6$ to $C_{24}$ aryl, and the substituents are independently selected from H, $C_1$ to $C_{18}$ alkyl and $C_1$ to $C_{18}$ alkoxy;
R[4], R[5], R[6] and R[7] are independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to C18 alkoxy.
A[4] to A[12] are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;
wherein
at least one of A[5] and/or A[6] are annelated with the ring system L1;
wherein
at least one of A[7] and/or A[8] and/or A[9] annelated with the ring system L2; and
wherein
formulas Ia to If of are connected at the position marked with "*" via a single bond; and wherein for the substituent Id: n=1 or 2, preferably 1.

According to an another embodiment an acridine compound of formula I, with a ring system K1 and K2 is provided:

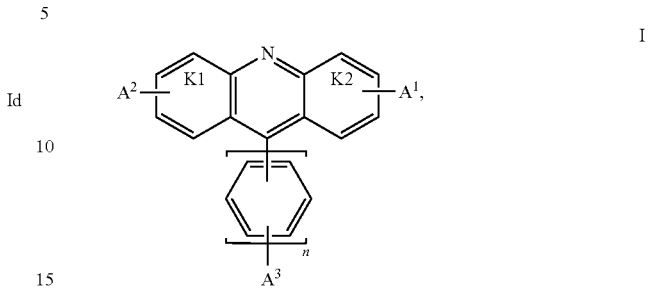

I wherein
n is 0, 1 or 2;
A[1] and A[2] are independently selected from H or aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of A[1] and/or A[2] are annelated with the ring system K2 or the ring system K1;
A[3] has the formulae Ia, having a ring system L1, or
has the formula Ib, having a ring system L2, or
has the formula Ic, or
has the formula Id, or
has the formula Ie, or
has the formula If:

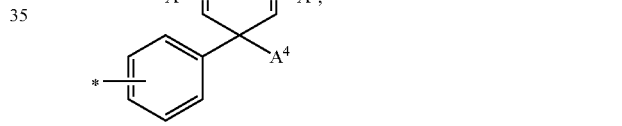

Ia

Ib

Ic

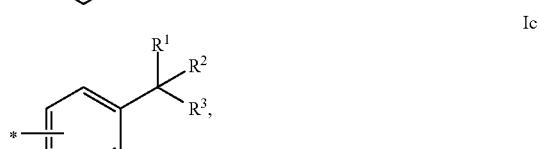

Id

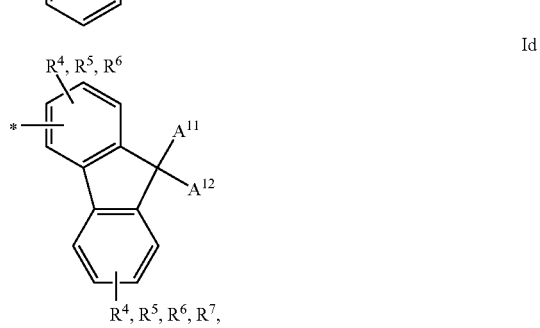

-continued

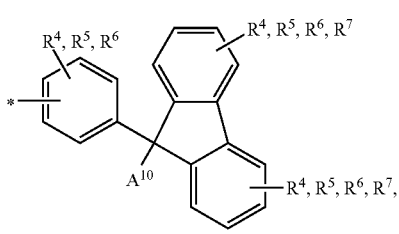
Ie

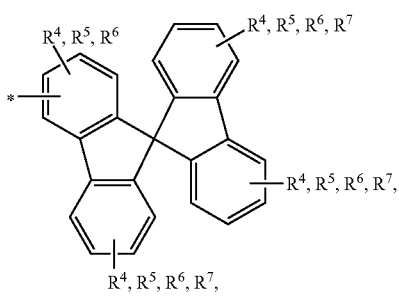
If

R¹, R² are independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy;

R³ is selected from unsubstituted or substituted $C_6$ to $C_{24}$ aryl, and the substituents are independently selected from H, $C_1$ to $C_{18}$ alkyl and $C_1$ to $C_{18}$ alkoxy;

R⁴, R⁵, R⁶ and R⁷ are independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

A⁴ to A¹² are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

wherein
at least one of A⁵ and/or A⁶ are annelated with the ring system L1;
wherein
at least one of A⁷ and/or A⁸ and/or A⁹ annelated with the ring system L2; and
wherein
formulas Ia to If of A³ are connected at the position marked with "*" via a single bond; and
wherein
for the substituent Id: n=1 or 2, preferably 1, and
for the substituent If: n=1 or 2, preferably 1.

According to an another embodiment an acridine compound of formula I, with a ring system K1 and K2 is provided:

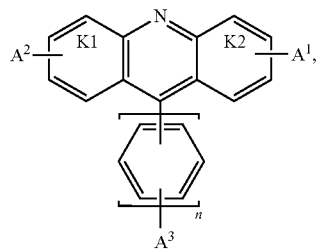
I wherein
n is 0, 1 or 2;
A¹ and A² are independently selected from H or aromatic cyclic ring of unsubstituted or substituted phenylene, and the substituents are selected from H, $C_1$ to C18 alkyl and $C_1$ to $C_{18}$ alkoxy, and at least one aromatic cyclic ring of A¹ and/or A² are annelated with the ring system K2 or the ring system K1;

A³ has the formulae Ia, having a ring system L1, or
has the formula Ib, having a ring system L2, or
has the formula Ic, or
has the formula Id, or
has the formula Ie, or
has the formula If:

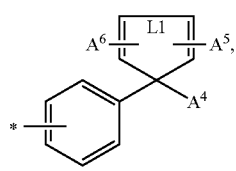
Ia

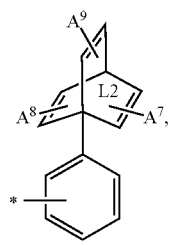
Ib

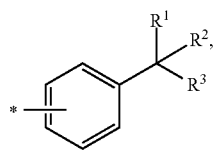
Ic

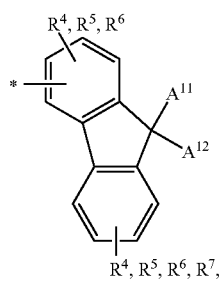
Id

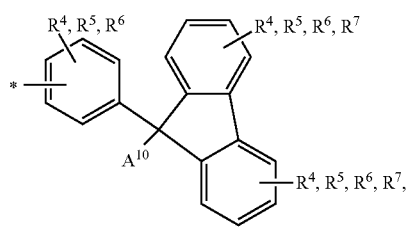
Ie

-continued

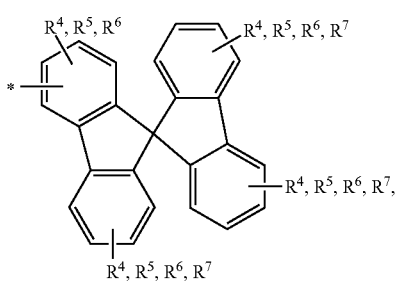

$R^1$, $R^2$ are independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy;

$R^3$ is selected from unsubstituted or substituted $C_6$ to $C_{24}$ aryl, and the substituents are independently selected from H, $C_1$ to $C_{18}$ alkyl and $C_1$ to $C_{18}$ alkoxy;

$R^4$, $R^5$, $R^6$ and $R^7$ are independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

$A^4$ to $A^{12}$ are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

wherein
at least one of $A^5$ and/or $A^6$ are annelated with the ring system L1;

wherein
at least one of $A^7$ and/or $A^8$ and/or $A^9$ annelated with the ring system L2; and wherein
formulas Ia to If of $A^3$ are connected at the position marked with "*" via a single bond; and wherein $R^4$, $R^5$, $R^6$ and $R^7$ exclude pyridyl, preferably $R^4$, $R^5$, $R^6$ and $R^7$ exclude unsubstituted pyridyl if n=0.

According to an another embodiment an acridine compound of formula I, with a ring system K1 and K2 is provided, wherein for formula (I):
n is 0, 1 or 2;
$A^1$ and $A^2$ are independently selected from H and or aromatic cyclic ring of unsubstituted or substituted phenylene, and the phenylene of $A^1$ and/or $A^2$ are annelated with the ring system K2 or the ring system K1,
$A^3$ has the formula selected from Ia, Ib, Ic, Id, Ie or If, wherein for formula (Ia):
  $A^4$, $A^5$ and $A^6$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy; wherein for formula (Ib):
  $A^7$, $A^8$ and $A^9$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula (Ic):
  $R^1$, $R^2$ are independently selected from unsubstituted or substituted $C_6$ to $C_{18}$ aryl and $C_1$ to $C_{18}$ alkyl, and the substituents are independently selected from H, $C_1$ to $C_{12}$ alkyl and $C_1$ to $C_{12}$ alkoxy;
  $R^3$ is selected from unsubstituted or substituted $C_6$ to $C_{18}$ aryl, and the substituents are independently selected from H, $C_1$ to $C_{12}$ alkyl and $C_1$ to $C_{12}$ alkoxy;

wherein for formula (Id), (Ie) and (If):
  are independently selected from H, unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy, and
  $A^{10}$, $A^{11}$, $A^{12}$ are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy; and
wherein
  for the substituent Id: n=1 or 2, preferably 1; and
  optional if n=0 then $R^4$, $R^5$, $R^6$ and $R^7$ exclude pyridyl, preferably unsubstituted pyridyl.

According to an another embodiment an acridine compound of formula I, with a ring system K1 and K2 is provided wherein n=1 or 2, preferably 1.

According to an another embodiment an acridine compound of formula I, with a ring system K1 and K2 is provided wherein the following compound is excluded:

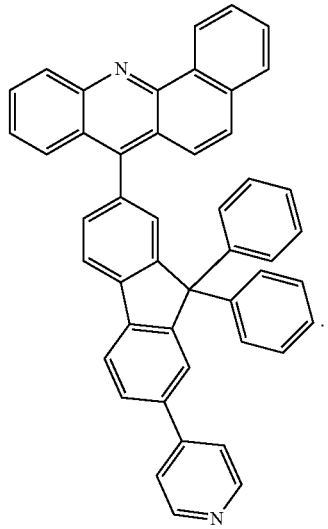 [SMILES: c1ccc(C2(c3ccccc3)c3cc(-c4ccncc4)ccc3-c3ccc(-c4c5ccccc5nc5c4ccc4ccccc45)cc32)cc1]

According to an another embodiment of the acridine compound of formula I, with the ring system K1 and K2, wherein the acridine compound of formula I comprises one N atom only.

According to an another embodiment of the acridine compound of formula I, with the ring system K1 and K2, wherein the acridine compound of formula I contains one N-atom and excludes additional hetero atoms.

According to an another embodiment of the acridine compound of formula I, with the ring system K1 and K2, wherein the acridine compound of formula I excludes a pyridyl-substituent.

According to an another embodiment of the acridine compound of formula I, with the ring system K1 and K2, wherein the substituents R4, R5, R6, R7 exclude an pyridyl, preferably exclude an unsubstituted pyridyl.

According to an another embodiment of the acridine compound of formula I, with the ring system K1 and K2, wherein the substituents R4, R5, R6, R7 are H.

According to an another embodiment of the acridine compound of formula I, with the ring system K1 and K2, wherein the acridine compound of formula I excludes a mono-benzoacridine with n=0 and $A^3$=Id and the substituents $R^4$, $R^5$, $R^6$, $R^7$ exclude an pyridyl, preferably exclude an unsubstituted pyridyl.

According to an another embodiment of the acridine compound of formula I, with the ring system K1 and K2, wherein $R^4$, $R^5$, $R^6$, $R^7$ is a pyridyl, preferably an unsubstituted pyridyl, then n=1 or 2.

According to an another embodiment of the acridine compound of formula I, with the ring system K1 and K2, wherein n=0 and $A^2$ is anellated with the ring K1 and $A^1$ is anellated with the ring K2.

According to an another embodiment of the acridine compound of formula I, with the ring system K1 and K2, wherein n=0, $A^1$ and $A^2$ are independently selected from aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of $A^1$ and/or $A^2$ are annelated with the ring system K2 or the ring system K1

According to an another embodiment of the acridine compound of formula I, with the ring system K1 and K2, wherein n=0, $A^1$ and $A^2$ are not H.

The compound represented by formula I, and a composition comprising the compound represented by formula I have strong electron transport characteristics to increase charge mobility and stability and thereby to improve luminance efficiency, voltage characteristics, and life-span characteristics. The compounds of formula I may be used in an electron transport layer, emission layer and/or hole injection layer. However the compounds of formula I may be preferably used in an electron transport layer.

In the present specification the wording "life span" and "life time" are synonymously used.

If not otherwise stated the Relative humidity (abbreviated RH) is 40% and the temperature is 23° C.

In the present specification, when a definition is not otherwise provided, "substituted" may refer to a substituent, which is independently selected from H, $C_1$ to $C_{18}$ alkyl and $C_1$ to $C_{18}$ alkoxy.

In the present specification, when a definition is not otherwise provided, an "alkyl group" may refer to an aliphatic hydrocarbon group. The alkyl group may refer to "a saturated alkyl group" without any double bond or triple bond.

The alkyl group may be a $C_1$ to $C_{18}$ alkyl group. More specifically, the alkyl group may be a $C_1$ to $C_{12}$ alkyl group, a $C_1$ to $C_6$ alkyl group or a $C_1$ to $C_4$ alkyl group. For example, a $C_1$ to $C_4$ alkyl group includes 1 to 4 carbons in an alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification "aryl group" may refers to a group including at least one hydrocarbon aromatic moiety, and all the elements of the hydrocarbon aromatic moiety may have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like.

The aryl group may include a monocyclic, polycyclic or fused ring polycyclic (i.e. rings sharing adjacent pairs of carbon atoms) functional group.

In the present specification, the single bond refers to a direct bond.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that an electron formed in the cathode may be easily injected into the emission layer and transported in the emission layer due to conductive characteristics according to a lowest unoccupied molecular orbital (LUMO) level.

According to another embodiment $R^1$, $R^2$ may be independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy, and preferably $R^1$, $R^2$ may be independently selected from unsubstituted or substituted $C_6$ to $C_{12}$ aryl, and the substituents are selected from H, $C_1$ to $C_{12}$ alkyl and $C_1$ to $C_{12}$ alkoxy.

According to another embodiment $R^3$ may be selected from unsubstituted or substituted $C_6$ to $C_{24}$ aryl, and the substituents are independently selected from H, $C_1$ to $C_{18}$ alkyl and $C_1$ to $C_{18}$ alkoxy, and preferably $R^3$ may be selected from unsubstituted or substituted $C_6$ to $C_{12}$ aryl, and the substituents are selected from H, $C_1$ to $C_{12}$ alkyl and $C_1$ to $C_{12}$ alkoxy.

According to another embodiment $A^1$ and $A^2$ may be independently selected from H, unsubstituted or substituted phenylene, and the substituents are selected from H, $C_1$ to $C_{18}$ alkyl and $C_1$ to $C_{18}$ alkoxy.

According to another embodiment $A^1$ and $A^2$ may be independently selected from H, unsubstituted or substituted phenylene, and the substituents are selected from H, $C_1$ to $C_{12}$ alkyl and $C_1$ to $C_{12}$ alkoxy.

According to another embodiment $A^1$ and $A^2$ are independently selected from H or aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of $A^1$ and/or $A^2$ are annelated with the ring system K2 or the ring system K1, wherein the unsubstituted or substituted phenylene is preferably a benzene ring.

According to another embodiment $A^1$ and $A^2$ may be independently selected from H or unsubstituted phenylene, wherein the unsubstituted or substituted phenylene is preferably a benzene ring.

According to another embodiment $A^4$, $A^5$, $A^6$, $A^7$, $A^8$, $A^9$, $A^{10}$, $A^{11}$ and $A^{12}$ may be independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

According to another embodiment $A^4$, $A^5$, $A^6$, $A^7$, $A^8$, $A^9$, $A^{10}$, $A^{11}$ and $A^{12}$ may be independently selected from unsubstituted or substituted $C_6$ to $C_{18}$ aryl, and the substituents are independently selected from H, $C_1$ to $C_{12}$ alkyl and $C_1$ to $C_{12}$ alkoxy.

According to another embodiment $A^4$, $A^5$, $A^6$, $A^7$, $A^8$, $A^9$, $A^{10}$, $A^{11}$ and $A^{12}$ may be independently selected from unsubstituted $C_6$ to $C_{12}$ aryl.

According to another embodiment $A^4$, $A^5$, $A^6$, $A^7$, $A^8$ and $A^9$ may be independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

According to another embodiment $A^4$, $A^5$, $A^6$, $A^7$, $A^8$ and $A^9$ may be independently selected from unsubstituted or substituted $C_6$ to $C_{18}$ aryl, and the substituents are independently selected from H, $C_1$ to $C_{12}$ alkyl and $C_1$ to $C_{12}$ alkoxy.

According to another embodiment $A^4$, $A^5$, $A^6$, $A^7$, $A^8$ and $A^9$ may be independently selected from unsubstituted $C_6$ to $C_{12}$ aryl.

In an embodiment $A^{10}$ to $A^{12}$ may be independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

In another embodiment $A^{10}$ to $A^{12}$ may be independently selected from unsubstituted $C_6$ to $C_{24}$ aryl and unsubstituted pyridyl.

In a further embodiment $A^{10}$ to $A^{12}$ may be independently selected from unsubstituted $C_6$ to $C_{18}$ aryl.

In a further embodiment $A^{10}$ to $A^{12}$ may be independently selected from unsubstituted $C_6$ to $C_{12}$ aryl.

In an embodiment $A^{10}$ to $A^{12}$ may be unsubstituted $C_6$ aryl.

According to another embodiment $R^4$, $R^5$, $R^6$ and $R^7$ may be independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

According to another embodiment $R^4$, $R^5$, $R^6$ and $R^7$ may be independently selected from H, unsubstituted or substituted $C_6$ to $C_{18}$ aryl, and the substituents are independently selected from H, $C_1$ to $C_{12}$ alkyl and $C_1$ to $C_{12}$ alkoxy.

According to another embodiment $R^4$, $R^5$, $R^6$ and $R^7$ may be independently selected from H or unsubstituted $C_6$ to $C_{12}$ aryl.

According to another embodiment "n" may be independently selected from 0, 1 or 2, preferably n=0 or 1 and in addition preferred n=0.

According to another embodiment an electronic device may include an anode and a cathode facing each other and at least one organic layer between the anode and the cathode, wherein the organic layer comprises or consists of the acridine compound according to formula I.

According to another embodiment the electronic device can be an organic optoelectronic device, an organic light emitting diode (OLED) or a photovoltaic cell, preferably the semiconductor device can be an organic light emitting diode (OLED).

According to another embodiment the electronic device, preferably an OLED, may include an anode and a cathode facing each other, at least one emission layer and at least one additional layer, wherein the at least one additional layer is arranged between the emission layer and the cathode, and wherein the at least one additional layer comprises or consists of the acridine compound according to formula I for an organic optoelectronic device.

According to yet another embodiment, an electronic device, preferably a display device, including at least one semiconductor layer comprising a compound of formula I according to the invention is provided.

The substituents of formulas Ia to Ie may result in a higher efficiency and/or longer lifetime compared with the substituent of formula If.

According to another aspect an acridine compound of formula I, with a ring system K1 and K2 is provided:

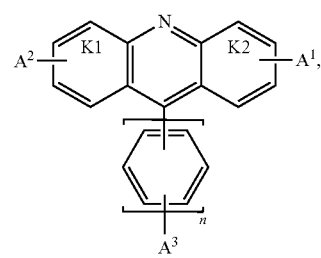

I wherein n is 0, 1 or 2;

$A^1$ and $A^2$ are independently selected from H or aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of $A^1$ and/or $A^2$ are annelated with the ring system K2 or the ring system K1;

$A^3$ has the formulae Ia, having a ring system L1, or has the formula Ib, having a ring system L2, or has the formula Ic, or has the formula Id, or has the formula Ie:

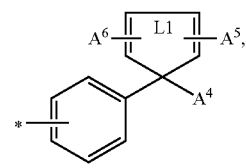

Ia

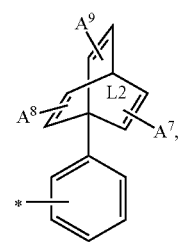

Ib

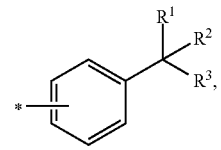

Ic

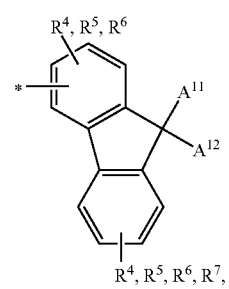

Id

-continued

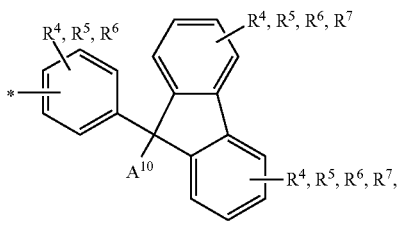

$R^1$, $R^2$ are independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy;

$R^3$ is selected from unsubstituted or substituted $C_6$ to $C_{24}$ aryl, and the substituents are independently selected from H, $C_1$ to $C_{18}$ alkyl and $C_1$ to $C_{18}$ alkoxy;

$R^4$, $R^5$, $R^6$ and $R^7$ are independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

$A^4$ to $A^{12}$ are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

wherein at least one of $A^5$ and/or $A^6$ are annelated with the ring system L1;

wherein at least one of $A^7$ and/or $A^8$ and/or $A^9$ annelated with the ring system L2; and wherein formulas Ia to Ie of $A^3$ are connected at the position marked with "*" via a single bond.

According to another aspect an acridine compound of formula I, with a ring system K1 and K2 is provided:

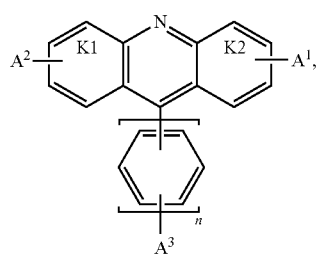

wherein n is 0, 1, or 2;

$A^1$ and $A^2$ are independently selected from H or aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of $A^1$ and/or $A^2$ are annelated with the ring system K2 or the ring system K1;

$A^3$ has the formulae Ia, having a ring system L1, or has the formula Ib, having a ring system L2, or has the formula Ic:

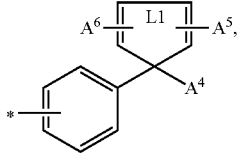

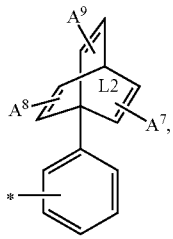

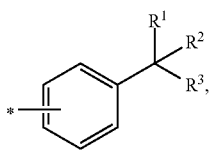

$R^1$, $R^2$ are independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy;

$R^3$ is selected from unsubstituted or substituted $C_6$ to $C_{24}$ aryl, and the substituents are independently selected from H, $C_1$ to $C_{18}$ alkyl and $C_1$ to $C_{18}$ alkoxy;

$A^4$ to $A^9$ are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

wherein at least one of $A^5$ and/or $A^6$ are annelated with the ring system L1;

wherein at least one of $A^7$ and/or $A^8$ and/or $A^9$ annelated with the ring system L2; and wherein formulas Ia to Ic of $A^3$ are connected at the position marked with "*" via a single bond.

According to another aspect an acridine compound of formula structure I, with a ring system K1 and K2:

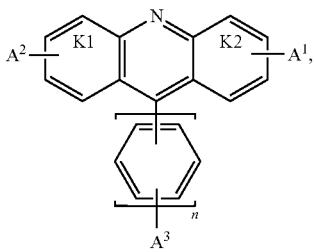

wherein
n is 0, 1 or 2;
A¹ and A² are independently selected from H or aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of A¹ and/or A² are annelated with the ring system K2 or the ring system K1;
A³ has the formula Id, or has the formula Ie:

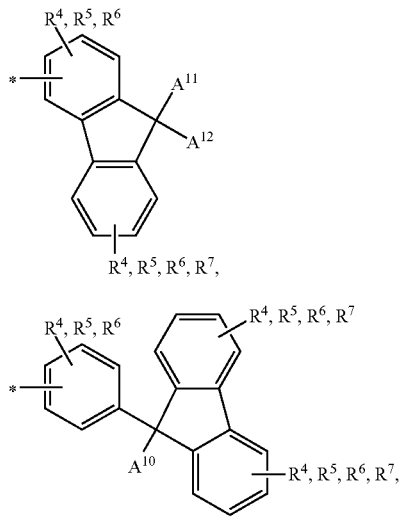

Id

Ie

R⁴, R⁵, R⁶ and R⁷ are independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.
A¹⁰ to A¹² are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;
wherein
formulas Id and Ie of A³ are connected at the position marked with "*" via a single bond.

According to another aspect A³ can have formulae Ia:

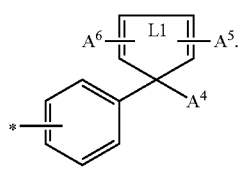

Ia

According to another aspect A³ can have formula Ib:

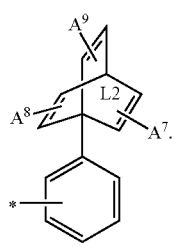

Ib

According to another aspect A³ can have formula Ic:

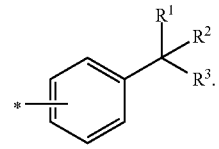

Ic

According to another aspect A³ can have formula Id:

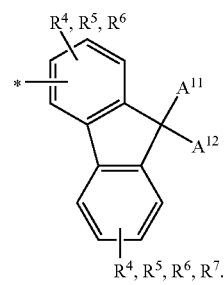

Id

According to another aspect A³ can have formula Ie:

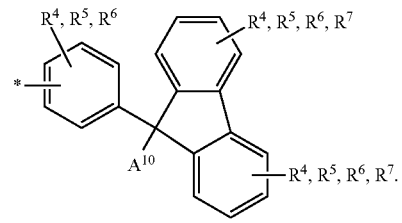

Ie

According to another aspect A³ can have formula If:

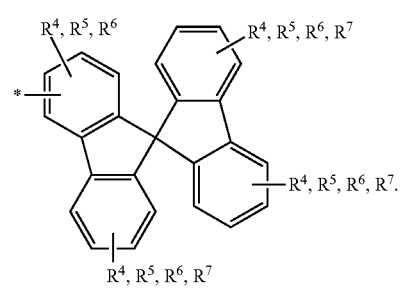

If

However, the substituents of Formulae Ia to Ie are more preferred. The substituent of formula If is less preferred.

According to another aspect an acridine compound of formula structure I, with a ring system K1 and K2 is provided:

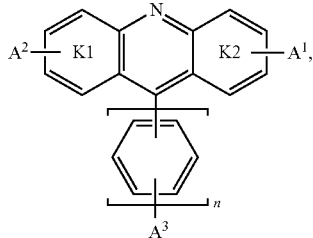

wherein n is 0, 1 or 2;

$A^1$ and $A^2$ are independently selected from H or aromatic cyclic ring of unsubstituted or substituted phenylene, preferably unsubstituted phenylene, and the substituents are selected from H, $C_1$ to $C_{18}$ alkyl and $C_1$ to $C_{18}$ alkoxy, and the phenylene of $A^1$ and/or $A^2$ are annelated with the ring system K2 or the ring system K1;

$A^3$ has the formulae Ia, having a ring system L1, or has the formula Ib, having a ring system L2, or has the formula Ic, or has the formula Id, or has the formula Ie:

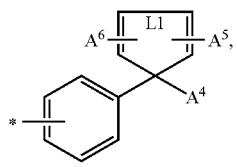

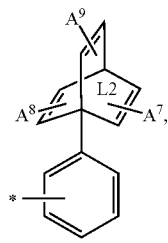

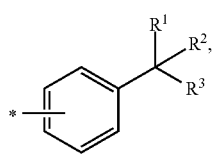

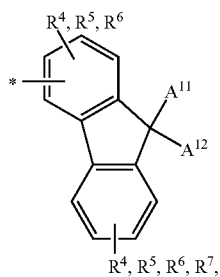

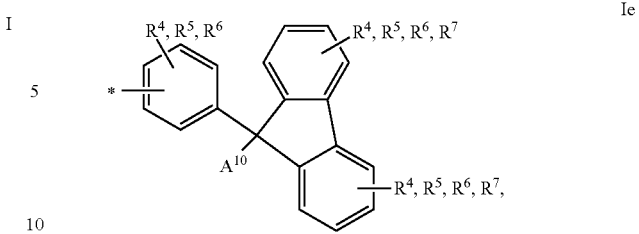

$R^1$, $R^2$ are independently selected from unsubstituted or substituted $C_6$ to $C_{18}$ aryl and $C_1$ to $C_{12}$ alkyl, and the substituents are independently selected from H, $C_1$ to $C_{12}$ alkyl and $C_1$ to $C_{12}$ alkoxy;

$R^3$ is selected from unsubstituted or substituted $C_6$ to $C_{18}$ aryl, and the substituents are independently selected from H, $C_1$ to $C_{12}$ alkyl and $C_1$ to $C_{12}$ alkoxy;

$R^4$, $R^5$, $R^6$ and $R^7$ are independently selected from H, unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy.

$A^4$ to $A^{12}$ are independently selected from unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy;

wherein at least one of $A^5$ and/or $A^6$ are annelated with the ring system L1;

wherein at least one of $A^7$ and/or $A^8$ and/or $A^9$ annelated with the ring system L2; and wherein formulas Ia to Ie of $A^3$ are connected at the position marked with "*" via a single bond.

According to another aspect an acridine compound is provided, wherein for formula I n is 0, 1 or 2, preferably 0 or 1;

$A^1$ and $A^2$ are independently selected from H and or aromatic cyclic ring of unsubstituted or substituted phenylene, and the phenylene of $A^1$ and/or $A^2$ are annelated with the ring system K2 or the ring system K1;

$A^3$ has the formula selected from Ia, Ib, Ic, Id, Ie, If or pefererably selected from Ia, Ib, Ic, Id or Ie;

wherein for formulae Ia:

$A^4$, $A^5$ and $A^6$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;

wherein for formula Ib:

$A^7$, $A^8$ and $A^9$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;

wherein for formula Ic:

$R^1$, $R^2$ are independently selected from unsubstituted or substituted $C_6$ to $C_{18}$ aryl and $C_1$ to $C_{18}$ alkyl, and the substituents are independently selected from H, $C_1$ to $C_{12}$ alkyl and $C_1$ to $C_{12}$ alkoxy;

$R^3$ is selected from unsubstituted or substituted $C_6$ to $C_{18}$ aryl, and the substituents are independently selected from H, $C_1$ to $C_{12}$ alkyl and $C_1$ to $C_{12}$ alkoxy;

wherein for formula Id, Ie and If:
$R^4$, $R^5$, $R^6$ and $R^7$ are independently selected from H, unsubstituted or substituted C6 to $C_{18}$ aryl and unsubstituted or substituted pyridyl, and the substituents are independently selected from H, $C_1$ to $C_{12}$ alkyl and $C_1$ to $C_{12}$ alkoxy, and
$A^{10}$, $A^{11}$, $A^{12}$ are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

According to another aspect an acridine compound is provided, wherein
for formula I
n is 0 or 1, preferably 1;
$A^1$ and $A^2$ are independently selected from H and or aromatic cyclic ring of unsubstituted or substituted phenylene, and the phenylene of $A^1$ and/or $A^2$ are annelated with the ring system K2 or the ring system K1;
$A^3$ has the formula selected from Ia, Ib, Ic, Id, Ie, If or preferrably selected from Ia, Ib, Ic, Id or Ie;
wherein for formulae Ia:
$A^4$, $A^5$ and $A^6$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula Ib:
$A^7$, $A^8$ and $A^9$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula Ic:
$R^1$, $R^2$ are independently selected from unsubstituted or substituted $C_6$ to $C_{18}$ aryl and $C_1$ to $C_{18}$ alkyl, and the substituents are independently selected from H, $C_1$ to $C_{12}$ alkyl and $C_1$ to $C_{12}$ alkoxy;
$R^3$ is selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula Id, Ie and/or If:
$R^4$, $R^5$, $R^6$ and $R^7$ are independently selected from H, unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy, and
$A^{10}$, $A^{11}$, $A^{12}$ are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy.

According to another aspect an acridine compound is provided, wherein
for formula I
n is 0, 1 or 2, preferably 1 or 2;
$A^1$ and $A^2$ are independently selected from H or unsubstituted phenylene, preferably unsubstituted phenylene, and the unsubstituted phenylene of $A^1$ and/or $A^2$ is annelated with the ring system K2 or the ring system K1;
$A^3$ has the formula selected from Ia, Ib, Ic, Id, Ie, If or preferrably selected from Ia, Ib, Ic, Id or Ie;
wherein for formulae Ia:
$A^4$, $A^5$ and $A^6$ are independently selected from unsubstituted $C_6$ to $C_{18}$ aryl;
wherein for formula Ib:
$A^7$, $A^8$ and $A^9$ are independently selected from unsubstituted $C_6$ to $C_{18}$ aryl;

wherein for formula Ic:
$R^1$, $R^2$ are independently selected from unsubstituted $C_6$ to $C_{18}$ aryl;
$R^3$ is selected from unsubstituted $C_6$ to $C_{18}$ aryl; wherein for formula Id and Ie:
$R^4$, $R^5$, $R^6$ and $R^7$ are independently selected from H, unsubstituted $C_6$ to $C_{18}$ aryl and unsubstituted pyridyl, and
$A^{10}$, $A^{11}$, $A^{12}$ are independently selected from unsubstituted $C_6$ to $C_{24}$ aryl and unsubstituted pyridyl.

According to another aspect an acridine compound is provided, wherein
for formula I
n is 0 or 1, preferably 1;
$A^1$ and $A^2$ are independently selected from H and phenylene and the phenylene of $A^1$ and/or $A^2$ are annelated with the ring system K2 or the ring system K1;
$A^3$ has the formula structure Ia, Ib, Ic, Id, Ie, If or pefererably selected from Ia, Ib, Ic, Id or Ie;
wherein for formulae Ia:
$A^4$, $A^5$ and $A^6$ are independently selected from unsubstituted $C_6$ to $C_{18}$ aryl;
wherein for formula Ib:
$A^7$, $A^8$ and $A^9$ are independently selected from unsubstituted $C_6$ to $C_{18}$ aryl;
wherein for formula Ic:
$R^1$, $R^2$ are independently selected from unsubstituted $C_6$ to $C_{18}$ aryl and $C_1$ to $C_{18}$ alkyl;
$R^3$ is selected from unsubstituted $C_6$ to $C_{18}$ aryl;
wherein for formula Id, Ie and/or If:
$R^4$, $R^5$, $R^6$ and $R^7$ are independently selected from H, unsubstituted $C_6$ to $C_{18}$ aryl,
$A^{10}$, $A^{11}$ and $A^{12}$ are independently selected from unsubstituted $C_6$ to $C_{18}$ aryl.

According to another aspect an acridine compound is provided, wherein
for formula I
n is 1 or 2, preferably 1;
$A^1$ and $A^2$ are independently selected from H and phenylene and the phenylene of $A^1$ and/or $A^2$ are annelated with the ring system K2 or the ring system K1;
$A^3$ has the formula structure Ia, Ib, Ic, Id, Ie, If or pefererably selected from Ia, Ib, Ic, Id or Ie;
wherein for formulae Ia:
$A^4$, $A^5$ and $A^6$ are independently selected from unsubstituted $C_6$ to $C_{12}$ aryl;
wherein for formula Ib:
$A^7$, $A^8$ and $A^9$ are independently selected from unsubstituted $C_6$ to $C_{12}$ aryl;
wherein for formula Ic:
$R^1$, $R^2$ are independently selected from unsubstituted $C_6$ to $C_{12}$ aryl and $C_1$ to $C_{12}$ alkyl;
$R^3$ is selected from unsubstituted $C_6$ to $C_{12}$ aryl;
wherein for formulae Ia, Ib, Ic, Id, Ie or If, preferably Ia, Ib, Ic, Id or Ie:
$R^4$, $R^5$, $R^6$ and $R^7$ are independently selected from H, unsubstituted $C_6$ to $C_{12}$ aryl,
$A^{10}$, $A^{11}$ and $A^{12}$ are independently selected from unsubstituted $C_6$ to $C_{12}$ aryl.

According to another aspect an acridine compound is provided, wherein
for formula I
n is 1 or 2, preferably 1;
$A^1$ and $A^2$ are independently selected from H and phenylene and the phenylene of $A^1$ and/or $A^2$ are annelated with the ring system K2 or the ring system K1;
$A^3$ has the formula structure Ia, Ib, Ic, Id, Ie, If or pefererably selected from Ia, Ib, Ic, Id or Ie;

wherein for formulae Ia:
A⁴, A⁵ and A⁶ are independently selected from H or unsubstituted C₆ aryl;
wherein for formula Ib:
A⁷, A⁸ and A⁹ are independently selected from H or unsubstituted C₆ aryl;
wherein for formula Ic:
R¹, R², R³ are independently selected from H or unsubstituted C₆ aryl;
wherein for formulae Ia, Ib, Ic, Id, Ie or If, preferably for formulae Ia, Ib, Ic, Id or Ie:
R⁴, R⁵, R⁶ and R⁷ are independently selected from H, or unsubstituted C₆ aryl,
A¹⁰, A¹¹ and A¹² are unsubstituted C₆ aryl.

According to an embodiment the acridine compounds can be selected from compounds having the chemical formula F1 to F5:

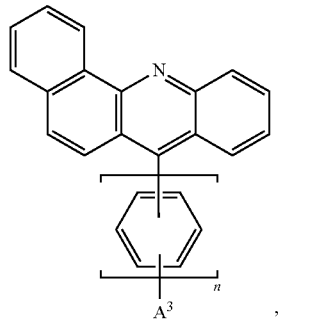

F1

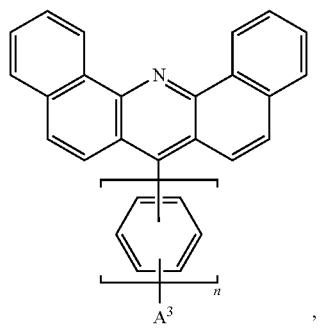

F2

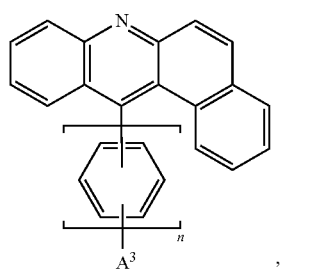

F3

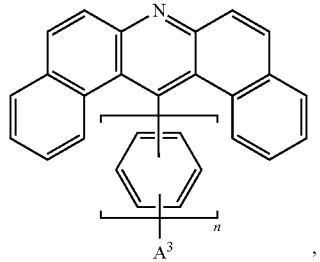

F4

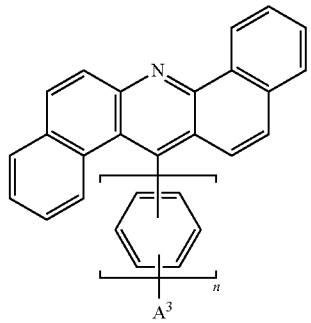

F5

According to another aspect the acridine compounds can be selected from compounds having the chemical formula F1 to F2:

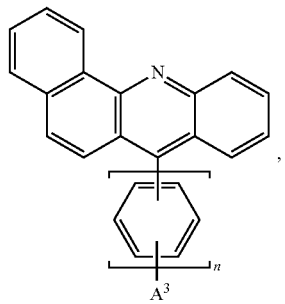

F1

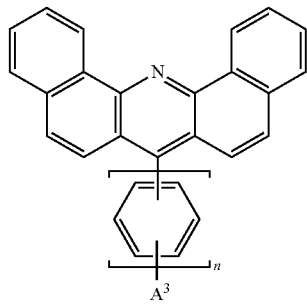

F2

According to another aspect the acridine compounds can be selected from compounds having the chemical formula F3 to F5:

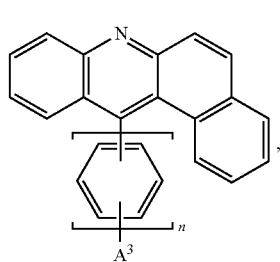

F3

F4
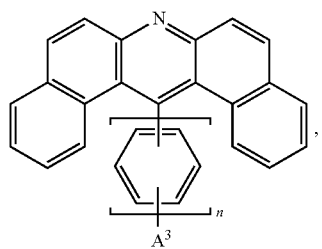
F5
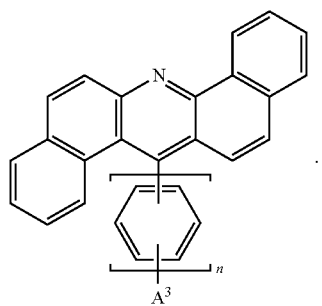
According to another aspect the acridine compounds can be selected from compounds having the chemical formula D1 to D16:
D1
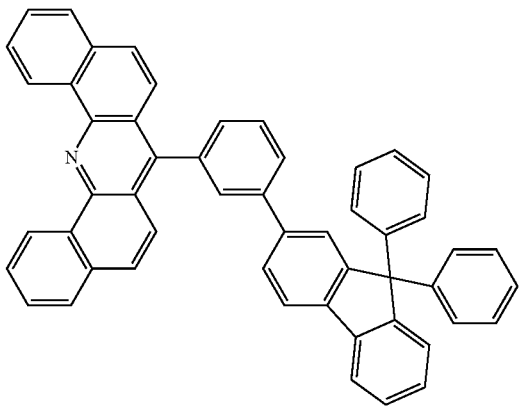
D2
D3
D4
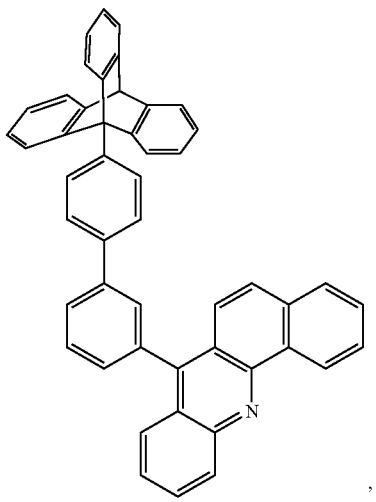
D5
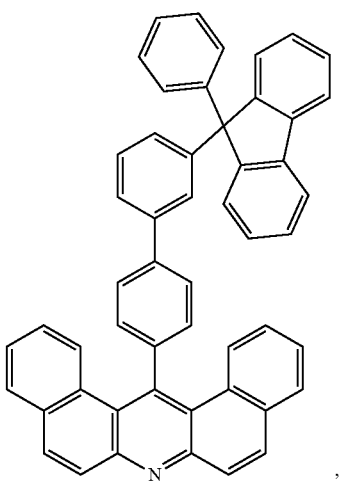

-continued
D6
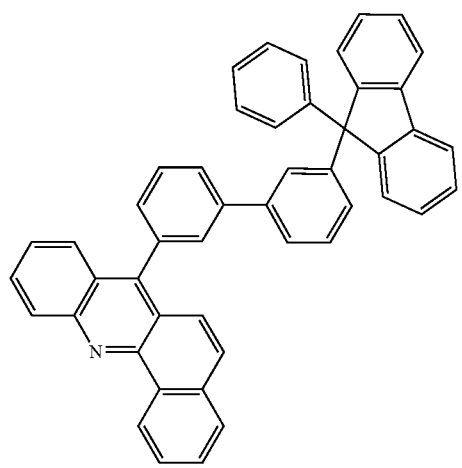
D7
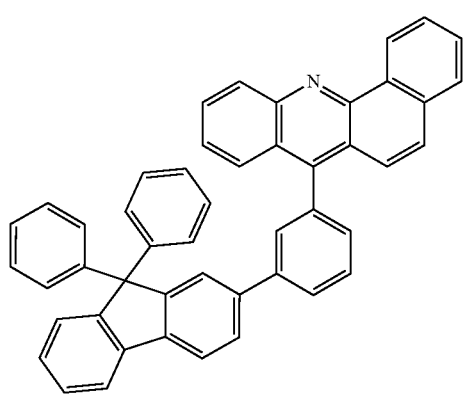
D8
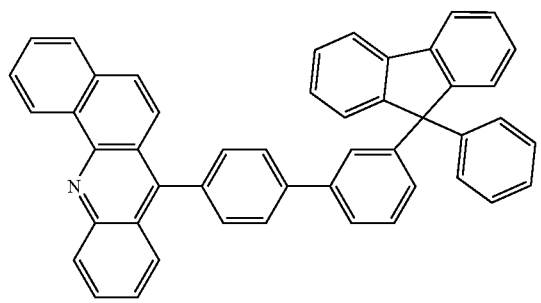
D9
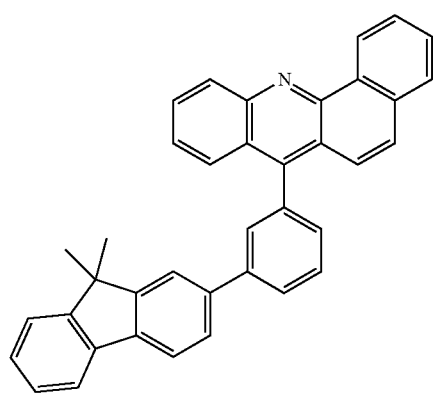
-continued
D10
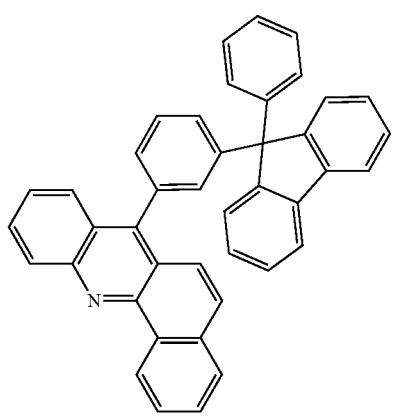
D11
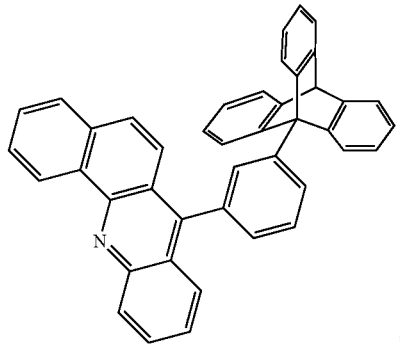
D12
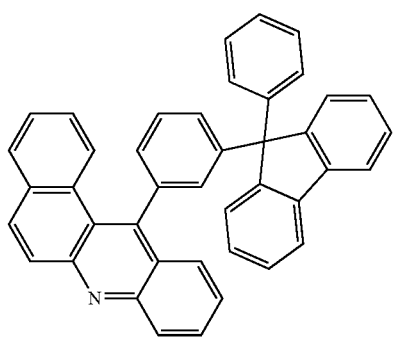
D13
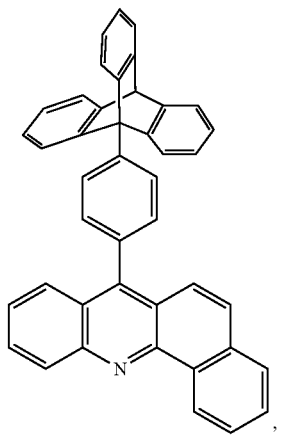

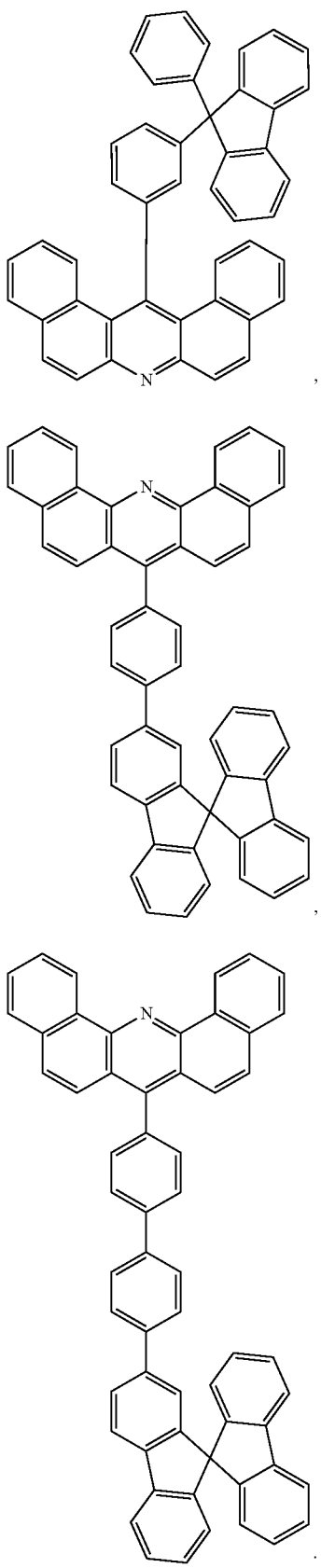

D14

D15

D16

According to another aspect the acridine compounds can be selected from compounds having the chemical formula D1 to D14.

According to another aspect the acridine compounds can be selected from compounds having the chemical formula D15 or D16.

According to another embodiment there is provided a semiconductor layer.

According to an embodiment the semiconductor layer may comprise or consist of at least one compound of formula I, preferably comprise or consist of at least one acridine compound of formulae D1 to D16 according to the invention.

The semiconductor layer comprising or consisting of an acridine compound of formula I, preferably of at least one acridine compound of formulae D1 to D16, is essentially non-emissive.

According to another embodiment the semiconductor layer is an organic semiconductor layer.

According to another embodiment the semiconductor layer is an electron transport layer.

According to another embodiment the semiconductor layer comprises in addition at least one alkali halide or alkali organic complex.

According to another embodiment an electronic device comprising at least one semiconductor layer comprising the compound of formula I is provided.

According to another embodiment a semiconductor device is provided, which comprises at least one semiconductor layer according to the invention.

The electronic device can be an organic electronic device.

According to an embodiment the electronic device, which can be preferably an OLED, may comprise a layer comprising or consisting of an acridine compound of formula I, or preferably of at least one acridine compound of formulae D1 to D16.

According to another embodiment the electronic device comprises at least one semiconductor layer comprising or consisting of an acridine compound of formula I, preferably of at least one acridine compound of formulae D1 to D16.

According to another embodiment the electronic device comprises at least one semiconductor layer comprising or consisting of an acridine compound of formula I, preferably of at least one acridine compound of formulae D1 to D16 and comprises in addition an alkali halide and/or an alkali organic complex.

The semiconductor layer can be an organic semiconductor layer.

According to another embodiment the electronic device comprises at least one semiconductor layer, wherein the semiconductor layer comprises or consists of an acridine compound of formula I, preferably of at least one acridine compound of formulae D1 to D16, wherein the semiconductor layer is a first electron transport layer.

According to another embodiment the electronic device can be an OLED, which comprises at least one semiconductor layer, wherein the semiconductor layer can be an electron transport layer that comprises a compound of formula I, or preferably of at least one acridine compound of formulae D1 to D16 or D1 to D14.

According to another embodiment the at least one electron transport layer may comprises in addition an alkali halide and/or alkali organic complex.

According to another embodiment the electronic device comprises at least one semiconductor layer that is a first electron transport layer.

According to another embodiment the electronic device, which is preferably an OLED, comprises at least one first electron transport layer, emission layer, anode electrode (anode layer) and a cathode electrode (cathode layer), wherein the electron transport layer comprises at least one compound of formula I, or preferably at least one acridine compound of formulae D1 to D16 or D1 to D14, and the first electron transport layer is arranged between the emission layer and the cathode electrode.

The wording "anode electrode" or "anode layer" have the same meaning.

The wording "cathode electrode" or "cathode layer" have the same meaning.

Preferably, the at least one electron transport layer is arranged between the emission layer and the cathode and is essentially non-emissive.

Preferably, the at least one electron transport layer is arranged between the emission layer and the cathode and is essentially non-emissive, wherein the electron transport layer, the emission layer and the cathode may differ in their components and/or composition, preferably in their components.

According to another embodiment, the electron transport layer, preferably the first electron transport layer, comprising the compound of formula I, or preferably at least one acridine compound of formulae D1 to D16 or D1 to D14, is in direct contact with the cathode electrode.

According to another embodiment, the electron transport layer comprising the compound of formula I, or preferably at least one acridine compound of formulae D1 to D16 or D1 to D14, preferably the first electron transport layer, is in direct contact with the emission layer.

According to another embodiment, the electron transport layer comprising the compound of formula I, or preferably at least one acridine compound of formulae D1 to D16 or D1 to D14.

According to another embodiment, the first electron transport layer comprising the compound of formula I, or preferably at least one acridine compound of formulae D1 to D16 or D1 to D14.

According to another embodiment, the first electron transport layer comprising the compound of formula I, or preferably at least one acridine compound of formulae D1 to D16 or D1 to D14, and the first electron transport layer is in direct contact with the second electron transport layer.

According to another embodiment, the electron transport layer comprising the compound of formula I, or preferably at least one acridine compound of formulae D1 to D16 or D1 to D14, preferably the first electron transport layer, is in direct contact with the electron injection layer.

According to another embodiment, the electron transport layer comprising the compound of formula I, or preferably at least one acridine compound of formulae D1 to D16 or D1 to D14, preferably the first electron transport layer, is contacting sandwiched between the electron transport layer and the electron injection layer.

According to another embodiment, the electron transport layer comprising the compound of formula I, or preferably at least one acridine compound of formulae D1 to D16 or D1 to D14, preferably the first electron transport layer, is contacting sandwiched between the electron transport layer and the electron injection layer and the semiconductor device further comprises an alkali halide or alkali organic complex.

According to another embodiment, the first electron transport layer comprising the compound of formula I, or preferably at least one acridine compound of formulae D1 to D16 or D1 to D14, is contacting sandwiched between a second electron transport layer and the cathode electrode.

According to another embodiment, the first electron transport layer comprising the compound of formula I, or preferably at least one acridine compound of formulae D1 to D16 or D1 to D14, is contacting sandwiched between the second electron transport layer and the cathode electrode and the semiconductor device further comprises an alkali halide or alkali organic complex.

According to another embodiment the electronic device can be a light emitting diode, a thin film transistor, a battery or a photovoltaic cell, preferably a light emitting device.

According to another embodiment the organic electronic device can be an organic light emitting diode, an organic thin film transistor, an organic battery or an organic photovoltaic cell, preferably an organic light emitting device.

According to another embodiment the electronic device can be an organic electroluminescent device.

According to another embodiment the electronic device can be a display device.

According to another embodiment the display device can be an organic display device.

The compound represented by formula I, or preferably at least one acridine compound of formulae D1 to D16 or D1 to D14 can be a host material of an emission layer or an electron transport layer or an hole injection layer.

The semiconductor device may realize a low driving voltage, high efficiency, high luminance and long life-span by including the organic layer including the compound for an organic optoelectronic device.

According to another embodiment a method of manufacturing the same is provided.

ADVANTAGEOUS EFFECTS

Surprisingly, it was found that the compounds of formula I and the inventive electronic device solve the problem underlying the present invention by being superior over the organic electroluminescent devices and compounds known in the art, in particular with respect to glass transition temperature, life time and cd/A efficiency.

The durability and performance of dibenzoacridine compounds used in organic electronic devices, for example as matrix material for an electron transport layer or as matrix material for emission layer, is important for the stability of such layers, especially in combination with other layers in the layer stack of an organic electronic device. An important parameter in the context of this stability that has been found by the inventors is the glass transition temperature (Tg) of the layer material. The Tg is often not high enough for sufficient layer stability over time and at operating elevated temperatures. Increasing the Tg of the layer material by modification of the molecular structure may go along with a deterioration of the charge transport properties of the layer and may lead to decreased device performance and lifetime.

A high glass transition temperature is important for improved thermal stability of a layer formed from the compound of formula I, and thereby improves thermal stability of an electronic device. High cd/A efficiency is important for high efficiency and thereby increased battery life of a mobile device, for example a mobile display device.

The inventors have surprisingly found that acridine compounds according to formula I have a significantly higher Tg (glass transition temperature).

Compounds of formula I according to the invention have an increased Tg (glass transition temperature) due to the sp3-hybridized carbon atom (spa-hybridized carbon atom=X) in the substituents Ia, Ib, Ic, Id, Ie and If.

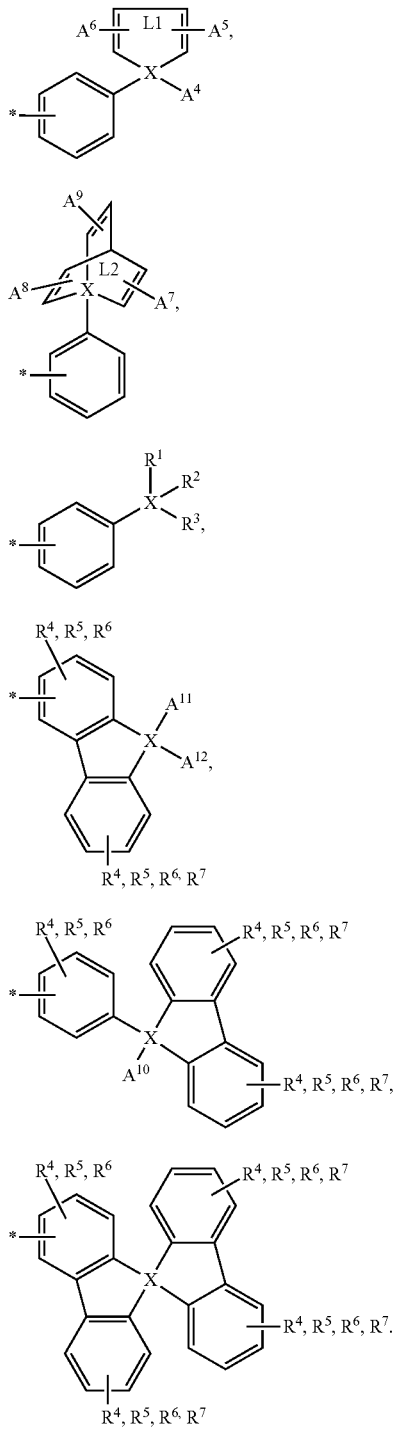

However, compounds of formula I with the substituents Ia, Ib, Ic, Id and/or Ie are more preferred.

Surprisingly, this molecular structure apparently does not impede the electron transport properties of the material. As a consequence the current efficiency and the lifetime of the OLED device is significantly enhanced.

Further OLEDs comprising a layer comprising a compound of formula 1 either as undoped or doped ETL show an increase in current efficiency (Ceff) and life time which is also unexpected.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned properties of cd/A efficiency. These compounds are discussed herein to be particularly preferred.

Further an organic optoelectronic device having high efficiency long life-span may be realized.

Hereinafter, a compound for an organic optoelectronic device according to an embodiment is described.

A compound for an organic optoelectronic device according to an embodiment is represented by formula I according to the invention.

The compound of the invention of formula I having an acridine structure element and a substituent of formula Ia to If, preferably Ia to Ie may help even though for injection or transport of holes or increases a glass transition temperature of the compound, and thus luminance efficiency may be increased due to suppression of an intermolecular interaction, and the compound may have a low deposition temperature relative to the molecular weight.

Without being bond to a specific theory, it is assumed, when the compound for an organic optoelectronic device represented by formula I forms a film, the compound may facilitate injection and transport of electrons in the device due to advantageous packing of the acridine structure element and the aryl groups connected via the sp$^3$-hybridized carbon atom having a more preferred structure compared to other acridine compounds with aromatic groups. With other words, due to the sp$^3$-hybridized carbon atom of the substituents of formula Ia to If, preferably Ia to Ie, the acridine compound of formula I becomes more bulky and the layer comprising the acridine compound of formula I becomes more amorphous. Therefore, when the compound for an organic optoelectronic device represented by formula I is particularly used to form an electron transport layer, an electron injection layer or an electron injection auxiliary layer, the compound may decrease a driving voltage of the device due to excellent electron transport characteristics and increase luminous efficiency due to good injection of electrons into an emission layer.

The compound for an organic optoelectronic device represented by formula I may include at least 4 to about 15, preferably at least 5 to about 8, substituted or unsubstituted $C_6$ to $C_{18}$ aryl groups. Particularly good performance characteristics are obtained when the compound of formula I may include at least 4 to about 15, preferably at least 5 to about 8, substituted or unsubstituted $C_6$ to $C_{18}$ aryl groups.

The acridine compounds represented by formula I may have a molecular weight (Mw) of ≥350 to ≤850 g/mol, and preferably ≥400 to ≤830 g/mol. If the molecular weight is selected for formula I in this range, particularly reproducible evaporation and deposition can be achieved in vacuum at temperatures where good long-term stability is observed.

In addition, the compound/s that can be used in an organic optoelectronic device may be represented preferably by one of formulae D1 to D16.

One or more of the compound/s of formula I, preferably of formulae D1 to D16, may be used for an organic optoelectronic device.

According to another aspect, the compound of formula I, preferably of formulae D1 to D16, may have a glass transition temperature (Tg) selected between ≥100 and ≤200° C., preferably ≥120 and ≤200° C., also preferred ≥140 and ≤200° C.

The glass transition temperature is measured under nitrogen and using a heating rate of 10 K per min in a Mettler Toledo DSC 822e differential scanning calorimeter as described in DIN EN ISO 11357, published in March 2010.

Preferably, the compound of formula I, preferably of formulae D1 to D16, are essentially non-emissive.

In the context of the present specification the term "essentially non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the dipole moment of the compound of formula I may be selected ≥0 and ≤2.8 Debye. Particularly good performance is obtained when the compound of formula I, preferably of formulae D1 to D16, is selected in this range.

The dipole moment $|\vec{\mu}|$ of a molecule containing N atoms is given by:

$$\vec{\mu} = \sum_{i}^{N} q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The partial charges and atomic positions are obtained using either the DFT functional of Becke and Perdew BP with a def-SV(P) basis or the hybrid functional B3LYP with a def2-TZVP basis set as implemented in the program package TURBOMOLE V6.5. If more than one conformation is viable, the conformation with the lowest total energy is selected to determine the dipole moment.

According to another aspect, the reduction potential of the compound of formula I, preferably of formulae D1 to D16, may be selected more negative than −2.1 V and less negative than −2.35 V against Fc/Fc$^+$ in tetrahydrofuran.

The reduction potential may be determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene In 0.1M concentration) as the standard. The average of potentials corresponding to cathodic and anodic peak of the studied compound, after subtraction of the average of cathodic and anodic potentials observed for the standard Fc$^+$/Fc redox couple, afforded finally the values reported above. All studied compounds as well as the reported comparative compounds showed well-defined reversible electrochemical behavior.

The present invention is further described in more detail.
Electron Transport Region/Electron Transport Layer An electron transport region of the stack of organic layers may be disposed on the emission layer.

The electron transport region of the stack of organic layers includes at least the first electron transport layer (first-ETL) and optional a second electron transport layer (second-ETL).

The first electron transport layer (first-ETL) is arranged closer to the cathode and the optional second electron transport layer (second-ETL) is arranged closer to the anode.

According to an embodiment an electron transport layer is provided, wherein the electron transport layer comprises at least one compound of formula I, preferably of formulae D1 to D16, according to the invention. Preferably the at least one first electron transport layer may comprise at least one compound of formula I, preferably of formulae D1 to D16, according to the invention.

According to another embodiment a semiconductor device is provided, preferably an OLED, comprising an electron transport layer, wherein the electron transport layer comprises at least one compound of formula I, preferably of formulae D1 to D16, according to the invention.

According to another embodiment a semiconductor device is provided, preferably an OLED, comprising at least two electron transport layers, wherein the first electron transport layer (first-ETL) comprises at least one compound of formula I, preferably of formulae D1 to D16, according to the invention.

According to an embodiment a semiconductor device is provided, preferably an OLED, comprising at least two electron transport layers, wherein the first electron transport layer (first-ETL) comprises at least one compound of formula I, preferably of formulae D1 to D16, according to the invention and the second electron transport layer (second-ETL) comprises at least one compound of formula I, preferably of formulae D1 to D16, according to the invention.

According to an embodiment a semiconductor device is provided, preferably an OLED, comprising at least two electron transport layers, wherein the first electron transport layer (first-ETL) comprises at least one compound of formula I, or preferably of at least one acridine compound of formulae D1 to D16, according to the invention and the second electron transport layer (second-ETL) comprises at least one compound of formula I, or preferably of at least one acridine compound of formulae D1 to D16, according to the invention, wherein the compound of formula I, or preferably of at least one acridine compound of formulae D1 to D16, of the first electron transport layer (first-ETL) are same or different with the compound of the second electron transport layer (second-ETL).

According to an embodiment a semiconductor device is provided, preferably an OLED, comprising at least two electron transport layers, wherein the first electron transport layer (first-ETL) comprises at least one compound of formula I, or preferably of at least one acridine compound of formulae D1 to D16, according to the invention and the second electron transport layer (second-ETL) comprises at least one compound of formula I according to the invention, wherein the compound of formula I of the first electron transport layer (first-ETL) is different from the compound of formula I of the second electron transport layer (second-ETL).

According to another embodiment the first electron transport layer (first-ETL) and/or the second electron transport layer (second-ETL) comprises in addition at least one alkali halide or alkali organic complex.

According to an embodiment a semiconductor device is provided, preferably an OLED, comprising at least two electron transport layers, wherein the first electron transport layer (first-ETL) comprises at least one compound of formula I, or preferably of at least one acridine compound of formulae D1 to D16, according to the invention and in addition at least one alkali halide or alkali organic complex; and the second electron transport layer (second-ETL) comprises at least one compound of formula I or 2 according to the invention and in addition at least one alkali halide or alkali organic complex, wherein the compound of formula I of the first electron transport layer (first-ETL) are same or different with the compound of formula I of the second electron transport layer (second-ETL); and wherein the at least one alkali halide or alkali organic complex of the first electron transport layer (first-ETL) are same or different with the at least one alkali halide or alkali organic complex of the second electron transport layer (second-ETL).

The first and second electron transport layer may differ in their composition and/or layer thickness.

According to an embodiment a semiconductor device is provided, preferably an OLED, comprising at least two electron transport layers, wherein the first electron transport layer (first-ETL) comprises at least one compound of formula I, or preferably of at least one acridine compound of formulae D1 to D16, according to the invention and in addition at least one alkali halide or alkali organic complex; and the second electron transport layer (second-ETL) comprises at least one compound of formula I according to the invention and in addition at least one alkali halide or alkali organic complex, wherein the compound of formula I of the first electron transport layer (first-ETL) is different from the compound of formula I of the second electron transport layer (second-ETL); and wherein the at least one alkali halide or alkali organic complex of the first electron transport layer (first-ETL) is different from the at least one alkali halide or alkali organic complex of the second electron transport layer (second-ETL).

According to an embodiment a semiconductor device is provided, preferably an OLED, comprising at least two electron transport layers, wherein the first electron transport layer (first-ETL) comprises at least one compound of formula I, or preferably of at least one acridine compound of formulae D1 to D16 or preferably at least one acridine compound of formulae D1 to D146, according to the invention and in addition at least one alkali halide or alkali organic complex; and the second electron transport layer (second-ETL) comprises at least one compound of formula I and is free of a alkali halide or alkali organic complex, wherein the compound of formula I of the first electron transport layer (first-ETL) are same or different, preferably different, from the compound of formula I of the second electron transport layer (second-ETL).

According to an embodiment a semiconductor device is provided, preferably an OLED, comprising at least two electron transport layers, wherein the first electron transport layer (first-ETL) comprises at least one compound of formula I according to the invention and in addition at least one alkali halide or alkali organic complex; and the second electron transport layer (second-ETL) does not comprise at least one compound of formula I and is free of a alkali halide or alkali organic complex.

The electron transport region of the stack of organic layers may further include an electron injection layer.

For example, the electron transport region of the stack of organic layers may have a structure of the electron injection layer/first electron transport layer (first-ETL) or as an alternative an electron injection layers/first electron transport layer (first-ETL)/second electron transport layer (second-ETL) but is not limited thereto. For example, an organic light emitting diode according to an embodiment of the present invention includes at least one electron transport layer, and in this case, the electron transport layer comprises a compound of formula I, or preferably of at least one acridine compound of formulae D1 to D16.

In another embodiment, the organic light emitting diode may comprise at least two electron transport layers in the electron transport region of the stack of organic layers, and in this case, the electron transport layer contacting the emission layer is defined as the second electron transport layer (second-ETL).

The electron transport layer may include one or two or more different electron transport matrix compounds.

The thickness of the first electron transport layer (first-ETL) may be from about 2 nm to about 100 nm, for example about 3 nm to about 30 nm. When the thickness of the first electron transport layer (first-ETL) is within these ranges, the first electron transport layer (first-ETL) may have improved electron transport auxiliary ability without a substantial increase in driving voltage.

A thickness of the optional second electron transport layer (second-ETL) may be about 0 nm to about 100 nm, for example about 5 nm to about 20 nm. When the thickness of the electron transport layer is within these ranges, the electron transport layer may have satisfactory electron transporting ability without a substantial increase in driving voltage.

Alkali Halide

Alkali halides, also known as alkali metal halides, are the family of inorganic compounds with the chemical formula MX, where M is an alkali metal and X is a halogen.

M can be selected from Li, Na, Potassium, Rubidium and Cesium.

X can be selected from F, Cl, Br and J.

According to various embodiments of the present invention a lithium halide may be preferred. The lithium halide can be selected from the group comprising LiF, LiCl, LiBr and LiJ. However, most preferred is LiF.

The alkali halides that are used are essentially non-emissive.

Alkali Organic Complex

According to various embodiments of the present invention the organic ligand of the alkali organic complex can be a quinolate.

The alkali organic complex that are used are essentially non-emissive.

According to various embodiments of the present invention the organic ligand of the alkali organic complex, preferably of a lithium organic complex, can be a quinolate.

Preferably the lithium organic complex is a lithium organic complex of formula III, IV or V:

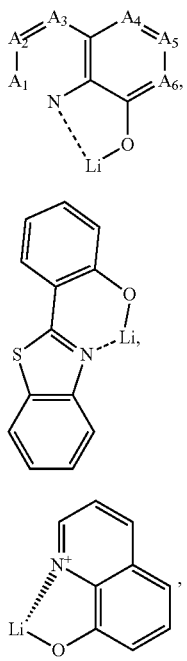

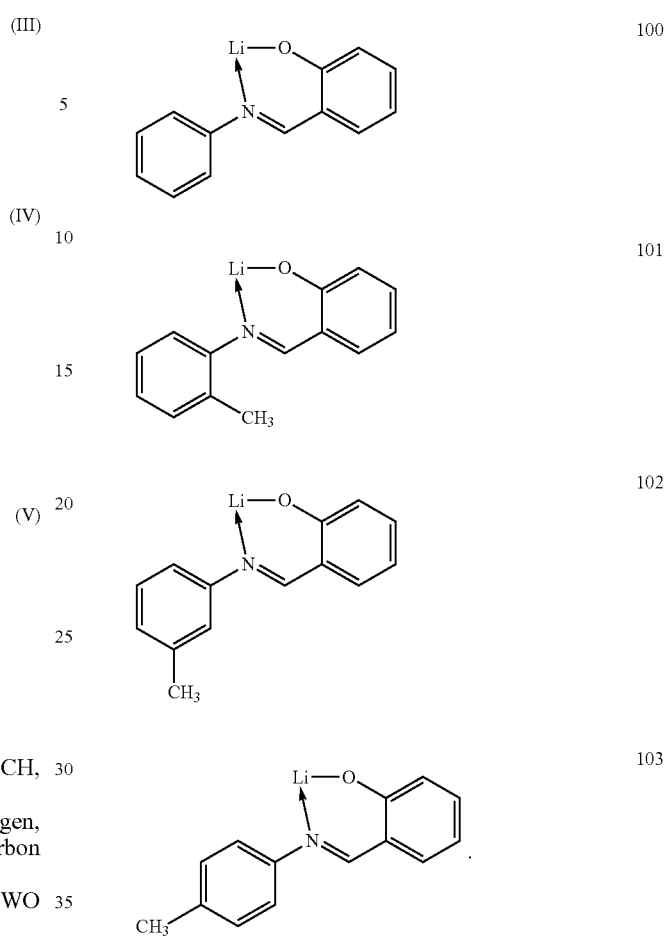

wherein

A1 to A6 are same or independently selected from CH, CR, N, O;

R is same or independently selected from hydrogen, halogen, alkyl or aryl or heteroaryl with 1 to 20 carbon atoms; and more preferred A1 to A6 are CH.

Quinolates that can be suitable used are disclosed in WO 2013079217 A1 and incorporated by reference.

According to various embodiments of the present invention the organic ligand of the lithium organic complex can be a borate based organic ligand, Preferably the lithium organic complex is a lithium tetra(1H-pyrazol-1-yl)borate. Borate based organic ligands that can be suitable used are disclosed in WO 2013079676 A1 and incorporated by reference.

According to various embodiments of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group of pyridinolate, preferably 2-(diphenylphosphoryl)pyridin-3-olate. Pyridine phenolate ligands that can be suitable used are disclosed in JP 2008195623 and incorporated by reference.

In addition, phenolate ligands can be selected from the group of imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group of oxazol phenolates, preferably 2-(benzo[d]oxazol-2-yl)phenolate. Oxazol phenolate ligands that can be suitable used are disclosed in US 20030165711 and incorporated by reference.

Lithium Schiff base organic complexes can be use. Lithium Schiff base organic complexes that can be suitable used having the structure 100, 101, 102 or 103:

According to various embodiments of the present invention the organic ligand of the lithium organic complex is a quinolate, a borate, a phenolate, a pyridinolate or a Schiff base ligand;

preferably the lithium quinolate complex has the formula III, IV or V:

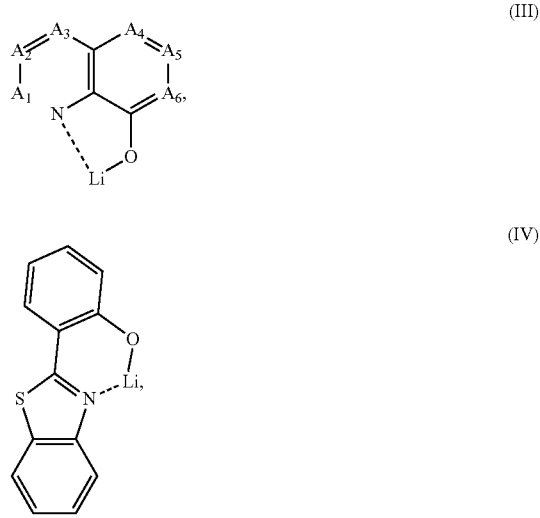

-continued

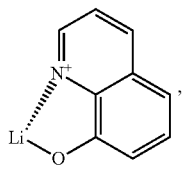

(V)

wherein
A1 to A6 are same or independently selected from CH, CR, N, O;
R is same or independently selected from hydrogen, halogen, alkyl or aryl or heteroaryl with 1 to 20 carbon atoms; and more preferred A1 to A6 are CH;
preferably the borate based organic ligand is a tetra(1H-pyrazol-1-yl)borate;
preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;
preferably the pyridinolate is a 2-(diphenylphosphoryl)pyridin-3-olate,
preferably the lithium Schiff base has the structure 100, 101, 102 or 103:

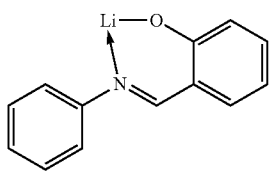

100

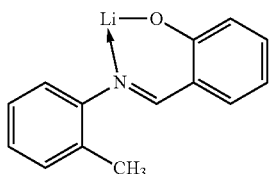

101

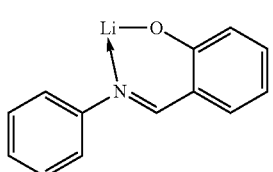

102

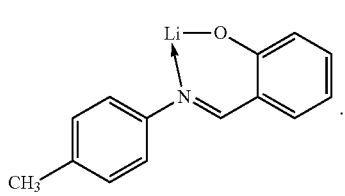

103

According to various embodiments of the present invention the first electron transport layer and/or the second electron transport layer, preferably the first electron transport layer, may comprises at least one compound of formula I according to the invention.

According to various embodiments the first and or second electron transport layer may comprises in addition a matrix compound.

Preferably the first electron transport layer comprises at least one compound of formula I according to the invention and the second electron transport layer comprises a matrix compound, which is selected different to the compound of formula I according to the invention, and may be selected from:
an anthracene based compound or a hetero substituted anthracene based compound, preferably 2-(4-(9,10-di(naphthalen-2-yl)anthracene-2-yl)phenyl)-1-phenyl-1H-benzo[d]imidazole and/or N4,N4"-di(naphthalen-1-yl)-N4,N4"-diphenyl-[1,1':4',1"-terphenyl]-4,4"-diamine;
a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide; or
a substituted phenanthroline compound, preferably 2,4,7,9-tetraphenyl-1,10-phenanthroline or 2,9-di(biphenyl-4-yl)-4,7-diphenyl-1,10-phenanthroline.

OLED

An OLED according to the invention may include an anode, a hole transport layer (HTL), an emission layer (EML), a first electron transport layer (ETL) comprising at least one compound of formula I according to the invention, and a cathode, which are sequentially stacked on a substrate. In this regard, the HTL, the EML, and the ETL are thin films formed from organic compounds.

According to various embodiments, the OLED may further include at least one layer selected from the group consisting of a hole injection layer (HIL), a hole transport layer, an emission layer, and a hole blocking layer, formed between the first anode electrode and the first electron transport layer, which comprises at least one compound of formula I according to the invention.

According to one embodiment the OLED may have the following layer structure, wherein the layers having the following order:
an anode, a hole injection layer comprising an organic matrix compound and a p-type dopant, a first undoped hole transport layer, a second undoped hole transport layer, emission layer comprising an organic matrix compound and an emitter dopant, optional a second undoped electron transport layer, a first electron transport layer comprising a compound of formula I according to the invention and a n-type dopant, an interlayer comprising an electron injection layer, and a cathode.

According to one embodiment the OLED may have the following layer structure according to table 1.

TABLE 1

| Layer structure of an OLED |
| --- |
| Cathode (transparent) |
| Interlayer (Electron Injection Layer) |
| Electron transport layer doped = Formula I according to the invention:n-type dopant |
| Electron transport layer (undoped) - optional |
| Emission layer = Mixed layer host:emitter dopant |
| Hole-transport layer (undoped) 2 |
| Hole-transport layer (undoped) 1 |
| Hole-injection layer (HIL) = Mixed layer host:p-type dopant |
| Anode |

According to another aspect of the present invention, there is provided a method of manufacturing an organic light-emitting diode (OLED), the method using:

at least one deposition source, preferably two deposition sources and more preferred at least three deposition sources.

The methods for deposition that can be suitable are comprising:
deposition via vacuum thermal evaporation;
deposition via solution processing, preferably the processing is selected from spin-coating, printing, casting; and/or
slot-die coating.

According to various embodiments of the present invention, there is provided a method using:
a first deposition source to release the compound of formula I according to the invention, and
a second deposition source to release the alkali halide or alkali organic complex, preferably a lithium halide or lithium organic complex;
the method comprising the steps of forming the electron transport layer stack; whereby for an organic light-emitting diode (OLED):
the first electron transport layer is formed by releasing the compound of formula I according to the invention from the first deposition source and the alkali halide or alkali organic complex, preferably a lithium halide or lithium organic complex from the second deposition source.

According to various embodiments of the present invention, the method may further include forming on the anode electrode an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
on a substrate a first anode electrode is formed,
on the first anode electrode an emission layer is formed,
on the emission layer an electron transport layer stack is formed, preferably the first electron transport layer is formed on the emission layer and optional a second electron transport layer is formed,
and finally a cathode electrode is formed,
optional a hole injection layer, a hole transport layer, and a hole blocking layer, formed in that order between the first anode electrode and the emission layer,
optional an electron injection layer is formed between the electron transport layer and the cathode electrode.

According to various embodiments of the present invention, the method may further include forming an electron injection layer on the first electron transport layer. However, according to various embodiments of the OLED of the present invention, the OLED may not comprise an electron injection layer.

According to various embodiments, the OLED may have the following layer structure, wherein the layers having the following order:
an anode, first hole transport layer, second hole transport layer, emission layer, optional second electron transport layer, first electron transport layer comprising a compound of formula I according to the invention, optional an interlayer comprising an electron injection layer, and a cathode.

Redox n-Dopant

Under redox n-dopant, it is understood a compound which, if embedded into an electron transport or electron injection layer, increases the concentration of free electrons in comparison with the neat matrix under the same physical conditions in a way that the conductivity of a layer comprising the redox-n-dopant is higher than the conductivity of the neat matrix layer.

The redox n-dopant does not emit light under the operation condition of an electroluminescent device, for example an OLED. In one embodiment, the redox n-dopant is selected from an electrically neutral metal complex and/or an electrically neutral organic radical.

The most practical benchmark for the strength of an n-dopant is the value of its redox potential. There is no particular limitation in terms how negative the value of the redox potential can be.

As redox potentials of usual electron transport matrices used in organic light emitting diodes are, if measured by cyclic voltammetry against ferrocene/ferrocenium reference redox couple, roughly in the range from about −1.8 V to about −3.1V; the practically applicable range of redox potentials for n-dopants which can effectively n-dope such matrices is in a slightly broader range, from about −1.7 V to about −3.3 V.

The measurement of redox potentials is practically performed for a corresponding redox couple consisting of the reduced and of the oxidized form of the same compound.

In case that the redox n-dopant is an electrically neutral metal complex and/or an electrically neutral organic radical, the measurement of its redox potential is actually performed for the redox couple formed by
(i) the electrically neutral metal complex and its cation radical formed by an abstraction of one electron from the electrically neutral metal complex, or
(ii) the electrically neutral organic radical and its cation formed by an abstraction of one electron from the electrically neutral organic radical.

Preferably, the redox potential of the electrically neutral metal complex and/or of the electrically neutral organic radical may have a value which is more negative than −1.7 V, preferably more negative than −1.9 V, more preferably more negative than −2.1 V, even more preferably more negative than −2.3 V, most preferably more negative than −2.5 V, if measured by cyclic voltammetry against ferrocene/ferrocenium reference redox couple for a corresponding redox couple consisting of
(i) the electrically neutral metal complex and its cation radical formed by an abstraction of one electron from the electrically neutral metal complex, or
(ii) the electrically neutral organic radical and its cation formed by an abstraction of one electron from the electrically neutral organic radical.

In a preferred embodiment, the redox potential of the n-dopant is between the value which is about 0.5 V more positive and the value which is about 0.5 V more negative than the value of the reduction potential of the chosen electron transport matrix.

Electrically neutral metal complexes suitable as redox n-dopants may be e.g. strongly reductive complexes of some transition metals in low oxidation state. Particularly strong redox n-dopants may be selected for example from Cr(II), Mo(II) and/or W(II) guanidinate complexes such as $W_2(hpp)_4$, as described in more detail in WO2005/086251.

Electrically neutral organic radicals suitable as redox n-dopants may be e.g. organic radicals created by supply of additional energy from their stable dimers, oligomers or polymers, as described in more detail in EP 1 837 926 B1, WO2007/107306, or WO2007/107356. Specific examples of such suitable radicals may be diazolyl radicals, oxazolyl radicals and/or thiazolyl radicals.

Under an elemental metal, it is understood a metal in a state of a neat metal, of a metal alloy, or in a state of free atoms or metal clusters. It is understood that metals deposited by vacuum thermal evaporation from a metallic phase, e.g. from a neat bulk metal, vaporize in their elemental form. It is further understood that if the vaporized elemental metal is deposited together with a covalent matrix, the metal atoms and/or clusters are embedded in the covalent matrix. In other words, it is understood that any metal doped covalent material prepared by vacuum thermal evaporation contains the metal at least partially in its elemental form.

For the use in consumer electronics, only metals containing stable nuclides or nuclides having very long halftime of radioactive decay might be applicable. As an acceptable level of nuclear stability, the nuclear stability of natural potassium can be taken.

In one embodiment, the n-dopant is selected from electropositive metals selected from alkali metals, alkaline earth metals, rare earth metals and metals of the first transition period Ti, V, Cr and Mn. Preferably, the n-dopant is selected from Li, Na, K, Rb, Cs, Mg, Ca, Sr, Ba, Sm, Eu, Tm, Yb; more preferably from Li, Na, K, Rb, Cs, Mg and Yb, even more preferably from Li, Na, Cs and Yb, most preferably from Li, Na and Yb.

The redox dopant may be essentially non-emissive.

Hole Injection Layer

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region includes a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Hole Transport Layer

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region includes the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in driving voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triaryl amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

The hole transport region of the stack of organic layers shall further include an electrical p-dopant improving conductivity and/or hole injection from the anode, in addition to the materials as described above.

Electrical p-Dopant

The charge-generating material may be homogeneously or inhomogeneously dispersed in the first hole transport layer.

The electrical p-dopant may be one of a quinone derivative, a radialene compound, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), radialene compounds like PD-2 and the like; metal oxides such as tungsten oxide, molybdenum oxide, and the like; and cyano-containing compounds such as compound HT-D1 below.

Compound HT-D1

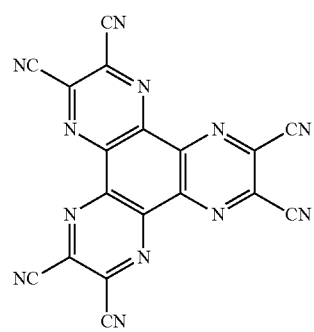

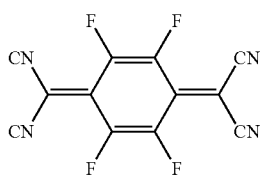
F4-TCNQ

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency.

Emission Layer

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

The emitter may be a red, green, or blue emitter.

In one embodiment, the emitter host material is a polar emitter host compound, which has a has a gas phase dipole moment in the range from about ≥0.2 Debye to about ≤2.0 Debye.

In one embodiment, the emitter host material is a polar emitter host compound having at least three aromatic rings, which are independently selected from carbocyclic rings and heterocyclic rings, which has a has a gas phase dipole moment in the range from about ≥0.2 Debye to about ≤2.0 Debye.

In one embodiment, the emitter host material is a polar emitter host compound represented by the chemical Formula 1:

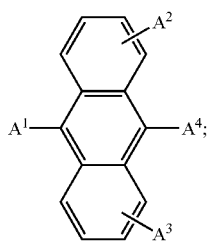
(1)

wherein

A$^1$ is selected from the group comprising a substituted or unsubstituted $C_6$-$C_{60}$ aryl or $C_6$-$C_{60}$ heteroaryl;

A$^2$ is selected from the group comprising a substituted or unsubstituted $C_1$ to $C_{10}$ alkyl group, a substituted or unsubstituted $C_6$-$C_{60}$ aryl or $C_6$-$C_{60}$ heteroaryl;

A$^3$ is selected from the group comprising a substituted or unsubstituted $C_1$ to $C_{10}$ alkyl group, a substituted or unsubstituted $C_6$-$C_{60}$ aryl or $C_6$-$C_{60}$ heteroaryl;

A$^4$ is selected from the group comprising a substituted or unsubstituted $C_6$-$C_{60}$ aryl or $C_6$-$C_{60}$ heteroaryl, preferably a $C_6$-$C_{60}$ heteroaryl.

Emitter Host

The polar emitter host compound has at least three aromatic rings, which are independently selected from carbocyclic rings and heterocyclic rings.

The polar emitter host compound has a gas phase dipole moment in the range from about ≥0.2 Debye to about ≤2.0 Debye.

According to one embodiment of electroluminescent device the polar emitter host compound has at least three aromatic rings, which are independently selected from carbocyclic rings and heterocyclic rings, and has a gas phase dipole moment in the range from about ≥0.2 Debye to about ≤2.0 Debye.

In another embodiment, the emitter host compound has a gas phase dipole moment in the range from about ≥0.3 Debye to about ≤1.8 Debye, preferably in the range from about ≥0.5 Debye to about ≤1.6 Debye, even more preferred in the range from about ≥0.6 Debye to about ≤1.4 Debye, and most preferred in the range from about ≥0.7 Debye to about ≤1.3 Debye.

If more than one conformation is viable, the conformation with the lowest total energy is selected to determine the dipole moment.

Electron Injection Layer

According to another aspect of the invention, the organic electroluminescent device may further comprise an electron injection layer between the first electron transport layer (first-ETL) and the cathode.

The electron injection layer (EIL) may facilitate injection of electrons from the cathode.

According to another aspect of the invention, the electron injection layer comprises:

(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or (ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer.

The electron injection layer may include at least one selected from LiF, NaCl, CsF, Li$_2$O, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in driving voltage.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device having a reflective anode deposited on a substrate, the cathode may be formed as a transmissive electrode from, for example, indium tin oxide (ITO) or indium zinc oxide (IZO).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm.

Electroluminescent Device

According to another embodiment of the electroluminescent device, wherein the first hole transport layer is arranged adjacent to the anode layer.

According to another embodiment of the electroluminescent device, wherein the electroluminescent device comprises in addition a second hole transport layer comprising a second hole transport matrix compound, preferably the second hole transport layer is formed of the second hole transport matrix compound, wherein the second hole transport layer is arranged between the first hole transport layer and the light emitting layer, and further preferred the second hole transport layer is adjacent arranged to the first hole transport layer and to the light emitting layer.

According to another embodiment, a display device is provided comprising at least one electroluminescent device according to the invention.

According to another embodiment, the hole transport region may contain a third hole transport layer which can be in direct contact with the emission layer.

According to another embodiment, the third hole transport layer can be in direct contact with the second hole transport layer.

According to another embodiment, the second electron transport layer (second-ETL) can be contacting sandwiched between the emission layer and the first electron transport layer (first-ETL).

According to another embodiment, the second electron transport layer (second-ETL) can be in direct contact with the emission layer.

According to another embodiment, the first electron transport layer (first-ETL) can be contacting sandwiched between the second electron transport layer (second-ETL) and the electron injection layer.

According to another embodiment, the first electron transport layer (first-ETL) can be in direct contact with the cathode electrode.

According to another embodiment, the second electron transport layer (second-ETL) can be contacting sandwiched between the first electron transport layer (first-ETL) and the cathode layer.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples. However, the present disclosure is not limited to the following examples

Figure 1:
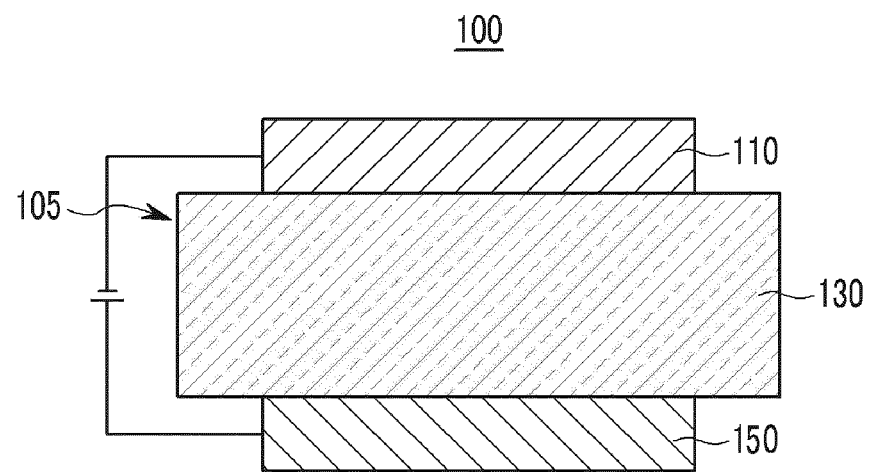
FIG. 1 is a cross-sectional view showing an organic light emitting diode according to an embodiment.

The compound for an organic optoelectronic device represented by formula I may be appropriate for an organic layer of an organic optoelectronic device, for example, a host or matrix material—also referred in the specification to as matrix compound—of an emission layer, an electron transport layer or an electron injection layer.

It is noted that the electron transport layer as well as the electron injection layer does not emit visible light (essentially non-emissive).

The organic optoelectronic device may realize a low driving voltage, high efficiency, high luminance and long life-span by including the organic layer including the compound for an organic optoelectronic device.

Hereinafter, the figures are illustrated in more detail with reference to examples. However, the present disclosure is not limited to the following figures.

FIGS. 1 to 4 are schematic cross-sectional views of organic light emitting diodes 100, 200, 300, and 400 according to an embodiment of the present invention. Hereinafter, referring to FIG. 1, a structure of an organic light emitting diode according to an embodiment of the present invention and a method of manufacturing the same are as follows. The organic light emitting diode 100 has a structure where a cathode 110, an organic layer 105 including an optional hole transport region; an emission layer 130 comprising a compound according to formula I; and an anode 150 that are sequentially stacked.

A substrate may be further disposed under the cathode 110 or on the anode 150. The substrate may be a substrate that is used in a general organic light emitting diode and may be a glass substrate or a transparent plastic substrate with strong mechanical strength, thermal stability, transparency, surface smoothness, ease of handling, and water resistance.

The anode 150 may be formed by depositing or sputtering an anode material on a substrate. The anode material may be selected from materials having a high work function that makes hole injection easy. The anode 150 may be a reflective electrode, a transflective electrode, or a transmissive electrode. The anode material may use indium tin oxide ITO), indium zinc oxide IZO), tin oxide ($SnO_2$), zinc oxide (ZnO), and the like. Or, it may be a metal such as magnesium (Mg), aluminum (Al), aluminum-lithium (Al-LI, calcium (Ca), magnesium-indium (Mg—In), or magnesium-silver (Mg—Ag).

The anode 150 may have a monolayer or a multi-layer structure of two or more layers. The organic light emitting diodes 100, 200, 300, and 400 according to an embodiment of the present invention may include a hole transport region; an emission layer 120; and a first electron transport layer 34 comprising a compound according to formula I.

Figure 2:
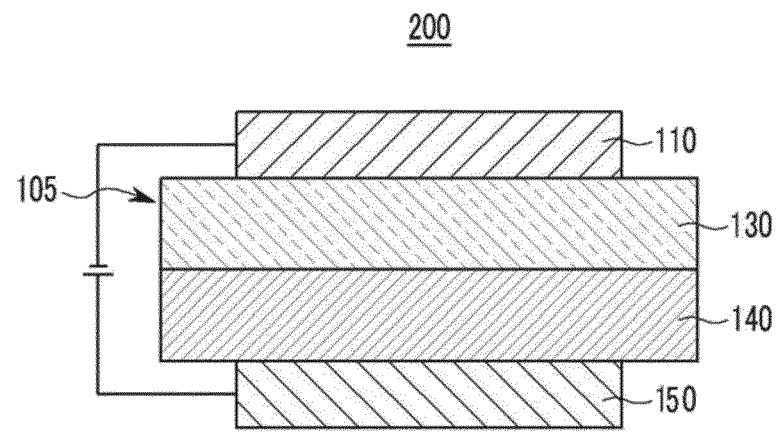
FIG. 2 is a cross-sectional view specifically showing an organic layer of an organic light emitting diode according to an embodiment.

For example, referring to FIG. 2, an organic light emitting diode according to an embodiment of the present invention is described. The organic light emitting diodes 100, 200, 300, and 400 according to an embodiment of the present invention may include further a hole auxiliary layer 140 between the anode 120 and the emission layer 130.

Figure 3:
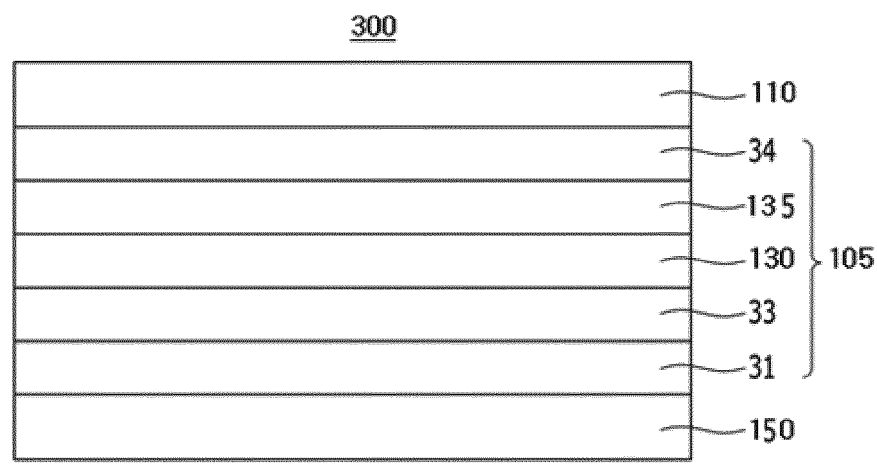
FIGS. 3 and 4 are cross-sectional views specifically showing a part of an organic layer of an organic light emitting diode according to an embodiment.

Referring to FIG. 3, the hole transport region 105 may include at least two layered hole auxiliary layer, and in this case, a hole auxiliary layer contacting the emission layer is defined as a hole transport auxiliary layer 33 and a hole auxiliary layer contacting an anode is defined as a hole transport layer 31 as well as two electron transport layer of electron transport layer (second-ETL) 135 comprising a compound according to formula I/first electron transport layer 34 comprising a compound of formula I, which is selected different with the compound according to formula I of the second electron transport layer. The hole transport region may include at least one of a hole injection layer, a hole transport layer, an electron blocking layer, and a buffer layer.

The hole transport region may include only hole injection layer or only hole transport layer. Or, the hole transport region may have a structure where a hole injection layer 37/hole transport layer 31 or hole injection layer 37/hole transport layer 31/electron blocking layer is sequentially stacked from the anode 120.

Figure 4:
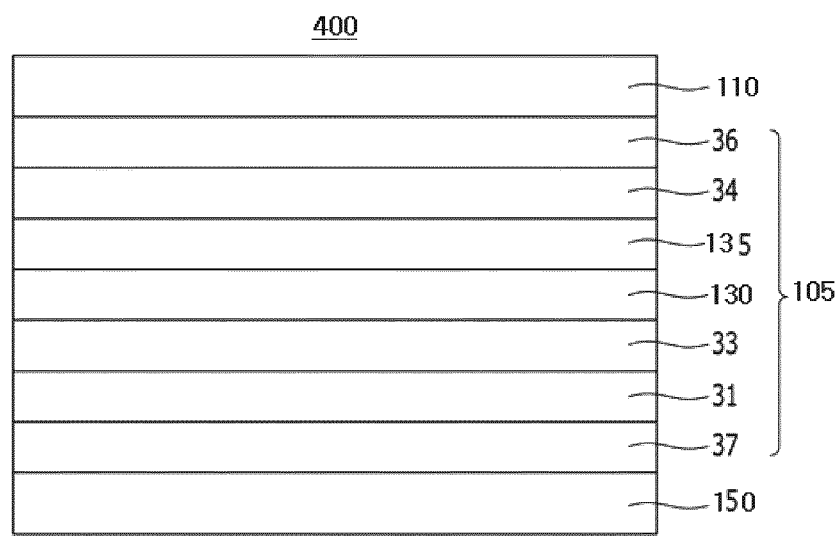

For example, the hole injection layer 37 and the electron injection layer 36 are additionally included and as shown in FIG. 4, anode 120/hole injection layer 37/hole transport layer 31/hole transport auxiliary layer 33/emission layer 130/second electron transport layer (second-ETL) 135 comprising a compound according to formula I/first electron transport layer 34 comprising a compound of formula I, which is selected different from the compound according to formula I of the second electron transport layer/electron injection layer 37/anode 110 are sequentially stacked.

In another example, the hole injection layer 37 and the electron injection layer 36 are additionally included and as shown in FIG. 4, anode 120/hole injection layer 37/hole transport layer 31/hole transport auxiliary layer 33/emission layer 130/second electron transport layer (second-ETL) 135 comprising a compound according to formula I/first electron transport layer 34 comprising a compound of formula I, which is selected different with the compound according to formula I of the second electron transport layer/electron injection layer 37/anode 110 are sequentially stacked.

The hole injection layer 37 may improve interface properties between ITO as an anode and an organic material used for the hole transport layer 31, and is applied on a non-planarized ITO and thus may planarize the surface of the ITO. For example, the hole injection layer 37 may include a material having a median value, particularly desirable conductivity between a work function of ITO and HOMO of the hole transport layer 31, in order to adjust a difference a work function of ITO as an anode and HOMO of the hole transport layer 31.

When the hole transport region includes a hole injection layer 37, the hole injection layer may be formed on the anode 150 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-8}$ torr to about $10^{-3}$ torr, and a deposition rate of about 0.01 to about 100 Å/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport region may be from about 100 Å to about 10000 Å, for example, about 100 Å to about 1000 Å. When the hole transport region includes the hole injection layer and the hole transport layer, a thickness of the hole injection layer may be from about 100 Å to about 10,000 Å, for example about 100 Å to about 1000 Å and a thickness of the hole transport layer may be from about 50 Å to about 2,000 Å, for example about 100 Å to about 1500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region. The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as compound HT-D1 below.

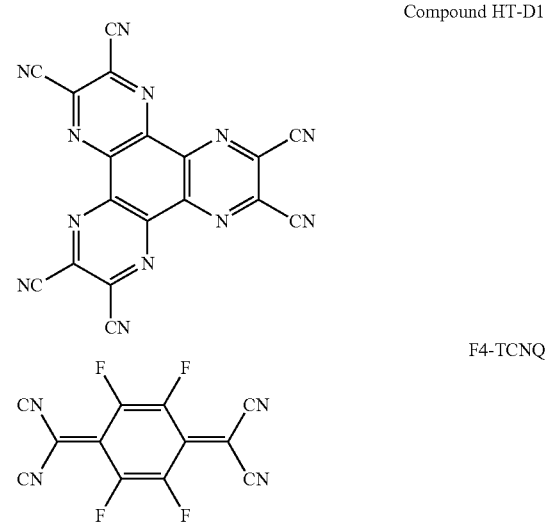

Compound HT-D1

F4-TCNQ

The hole transport region may further include a buffer layer.

The buffer layer may compensate for an optical resonance distance of light according to a wavelength of the light emitted from the EML, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include a host and a dopant.

For example, the composition comprising compound of formula I may be used as a light-emitting material for an organic optoelectronic device such as an OLED. Herein, the compound of formula I may be used as the emitter host (also named EML host), and may further include at least one dopant. The dopant may be a red, green, or blue dopant.

Other compounds that can be used as the emitter host is an anthracene matrix compound represented by formula 400 below:

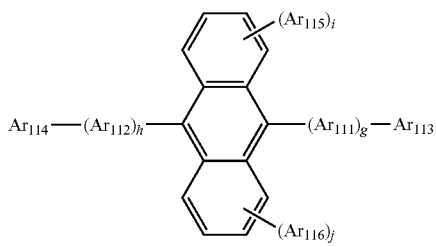

Formula 400

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ aryl group; and g, h, i, and j may be each independently an integer from 0 to 4.

In some embodiments, $Ar_{111}$ and $Ar_{112}$ in formula 400 may be each independently one of a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of
- a $C_1$-$C_{10}$ alkyl group substituted with at least one of a phenyl group, a naphthyl group, or an anthryl group;
- a phenyl group, a naphthyl group, an anthryl group, a pyrenyl group, a phenanthrenyl group, or a fluorenyl group;
- a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof,
- a sulfonic acid group or a salt thereof, a phosphoric acid group or a salt thereof,
- a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group

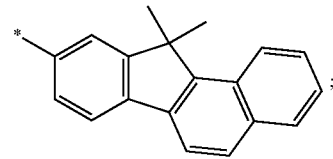 [SMILES: *c1ccc2c(c1)C(C)(C)c1c-2ccc2ccccc12]

or formulas 2 or 3

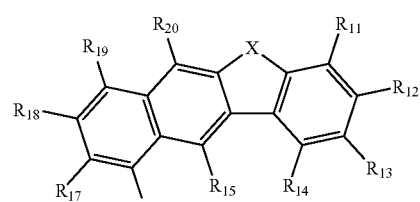

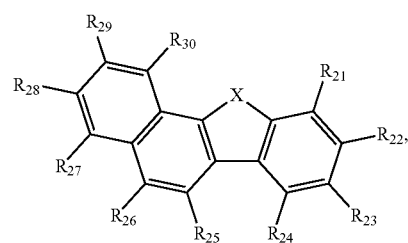

Wherein in the formulas 2 and 3, X is selected form an oxygen atom and a sulfur atom, but embodiments of the invention are not limited thereto.

In the formula 2, any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula 3, any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

Preferably, the dipole moment of the EML host is selected ≥0.2 Debye and ≤1.45 Debye, preferably ≥0.4 Debye and ≤1.2 Debye, also preferred ≥0.6 Debye and ≤1.1 Debye.

The dipole moment is calculated using the optimized using the hybrid functional B3LYP with the 6-31G* basis set as implemented in the program package TURBOMOLE V6.5. If more than one conformation is viable, the conformation with the lowest total energy is selected to determine the dipole moment of the molecules. Using this method, 2-(10-phenyl-9-anthracenyl)-benzo[b]naphtho[2,3-d]furan (CAS 1627916-48-6) has a dipole moment of 0.88 Debye, 2-(6-(10-phenylanthracen-9-yl)naphthalen-2-yl)dibenzo[b,d]thiophene (CAS 1838604-62-8) of 0.89 Debye, 2-(6-(10-phenylanthracen-9-yl)naphthalen-2-yl)dibenzo[b,d]furan (CAS 1842354-89-5) of 0.69 Debye, 2-(7-(phenanthren-9-yl)tetraphen-12-yl)dibenzo[b,d]furan (CAS 1965338-95-7) of 0.64 Debye, 4-(4-(7-(naphthalen-1-yl)tetraphen-12-yl)phenyl) dibenzo[b,d] furan (CAS 1965338-96-8) of 1.01 Debye.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be a fluorescent dopant, for example ter-fluorene, the structures are shown below. 4.4'-bis(4-diphenyl amiostyryl)biphenyl (DPAVBI, 2,5,8,11-tetra-tert-butyl perylene (TBPe), and Compound 4 below are examples of fluorescent blue dopants.

Compound 4

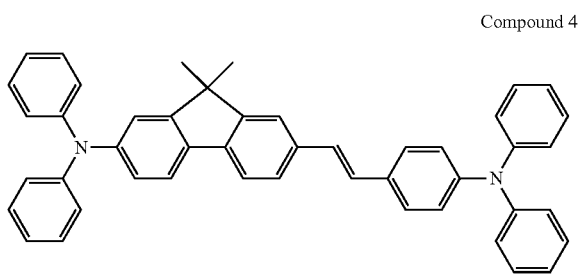 [SMILES: CC1(C)c2cc(/C=C/c3ccc(N(c4ccccc4)c4ccccc4)cc3)ccc2-c2ccc(N(c3ccccc3)c3ccccc3)cc21]

The dopant may be a phosphorescent dopant, and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$$L_2MX \quad (Z).$$

In formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

A thickness of the emission layer may be about 100 Å to about 1000 Å, for example about 200 Å to about 600 Å. When the thickness of the emission layer is within these ranges, the emission layer may have improved emission characteristics without a substantial increase in a driving voltage.

Next, an electron transport region is disposed on the emission layer.

The electron transport region may include at least one of a second electron transport layer, a first electron transport layer, and an electron injection layer.

For example, the electron transport region may have a structure of a second electron transport layer/first electron transport layer/electron injection layer or first electron transport layer/electron injection layer, but is not limited thereto. For example, an organic light emitting diode according to an embodiment of the present invention includes at least two electron transport layers in the electron transport region, and in this case, an electron transport layer contacting the emission layer is defined as an electron transport layer (second-ETL) 135.

The electron transport layer (second-ETL) may have a monolayer or multi-layer structure including two or more different materials.

The electron transport region may include at least one compound represented by formula I. For example, the electron transport region may include an electron transport layer (second-ETL), and the electron transport layer (second-ETL) may include the compound for an organic optoelectronic device represented by formula I. More specifically, the electron transport layer (second-ETL) 135 may include the compound for an organic optoelectronic device represented by formula I.

According to another aspect of the present invention, the electron transport layer (second-ETL) 135 consists of compound of formula I.

The formation conditions of the electron transport layer (second-ETL) 135, electron transport layer (first-ETL) 34, and electron injection layer 36 of the electron transport region refers to the formation condition of the hole injection layer.

When the electron transport region includes the electron transport layer (second-ETL) 135, the electron transport layer may include at least one of BCP, Bphen, and BAlq, but is not limited thereto.

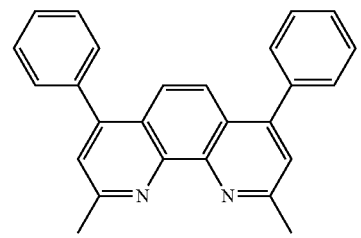

BCP

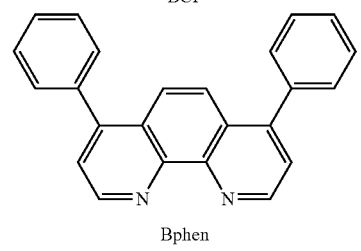

Bphen

The thickness of the electron transport layer may be from about 20 Å to about 1000 Å, for example about 30 Å to about 300 Å. When the thickness of the electron transport layer is within these ranges, the electron transport layer may have improved electron transport auxiliary ability without a substantial increase in driving voltage.

According to another aspect of the present invention, the electron transport layer (first-ETL) 34 comprises a compound of formula I.

According to another aspect of the present invention, the first electron transport layer 34 comprises a compound of formula I and further comprises an alkali halide and/or alkali organic complex.

The first or second electron transport layer may include in addition at least one of the BCP, Bphen and the following Alq₃, Balq, TAZ and NTAZ;

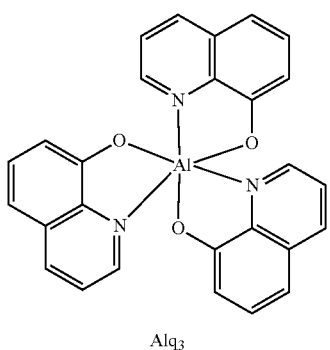

Alq₃

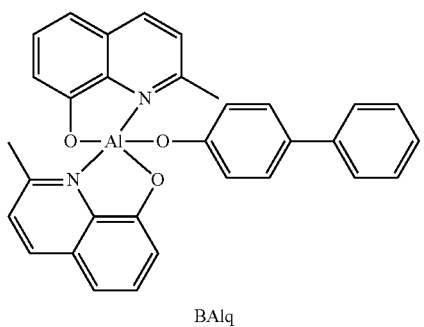

BAlq

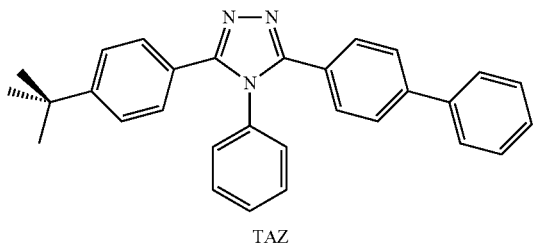

TAZ

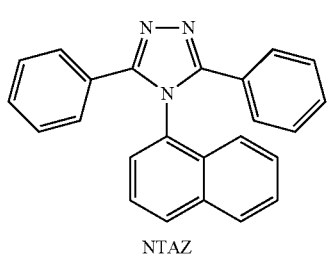

NTAZ or, the electron transport layer may include at least one of the following compounds ET1 and ET2, but is not limited thereto:

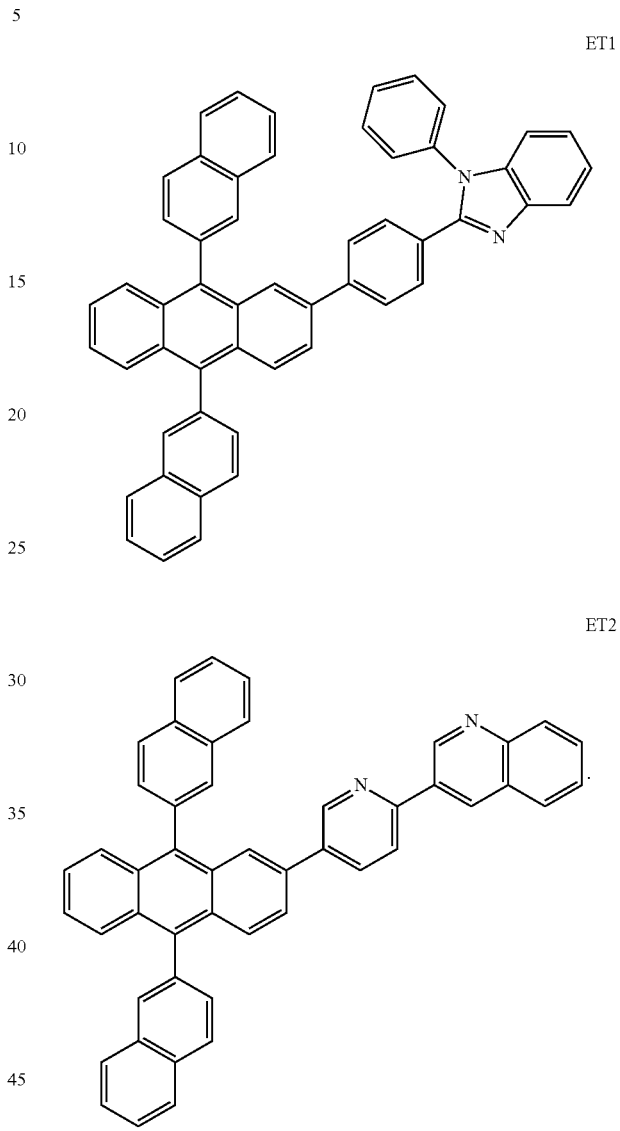

A thickness of the electron transport layer may be about 100 Å to about 1000 Å, for example about 150 Å to about 500 Å. When the thickness of the electron transport layer is within these ranges, the electron transport layer may have satisfactory electron transporting ability without a substantial increase in driving voltage.

The second electron transport layer 135 may further include an alkali metal halide and/or alkali organic complex, in addition to the above-described materials. Preferably, the second electron transport layer 135 comprises an alkali organic complex.

Preferably the second electron transport layer is free of a metal, an alkali metal halide and/or alkali organic complex.

The alkali organic complex may include a lithium (Li organic complex). The Li complex may include, for example, the following compound ET-D1 (lithium quinolate, LiQ) or ET-D2.

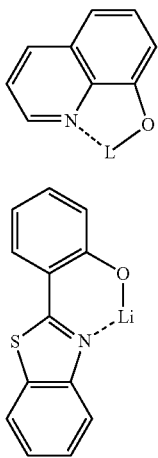

ET-D1

ET-D2

The alkali halide may be selected from the group consisting of LiF, LiCl, LiBr, LiI NaF, NaCl, NaBr, NaI, KF, KBr and CsF.

In addition, the electron transport region may include an electron injection layer (EIL) 36 that may facilitate injection of electrons from the anode 110.

The electron injection layer 36 is disposed on an electron transport layer and may play a role of facilitating an electron injection from a cathode and ultimately improving power efficiency and be formed by using any material used in a related art without a particular limit, for example, LiF, Liq, NaCl, CsF, $Li_2O$, BaO, Yb and the like.

The electron injection layer may include at least one selected from LiF, NaCl, CsF, $Li_2O$, and BaO.

A thickness of the EIL may be from about 1 Å to about 100 Å, or about 3 Å to about 90 Å. When the thickness of the electron injection layer is within these ranges, the electron injection layer may have satisfactory electron injection ability without a substantial increase in driving voltage.

The anode 150 is disposed on the organic layer 105. A material for the anode 150 may be a metal, an alloy, or an electrically conductive compound that have a low work function, or a combination thereof. Specific examples of the material for the anode 150 may be lithium (LI, magnesium (Mg), aluminum (Al), aluminum-lithium (Al-LI, calcium (Ca), magnesium-indium (Mg—In), magnesium-silver (Mg—Ag), etc. In order to manufacture a top-emission light-emitting device, the anode 150 may be formed as a transmissive electrode from, for example, indium tin oxide ITO) or indium zinc oxide IZO).

According to another aspect of the invention, a method of manufacturing an organic electroluminescent device (400) is provided, wherein on an anode electrode the other layers of hole injection layer (37), hole transport layer (31), optional an electron blocking layer (33), an emission layer (130), first electron transport layer (first-ETL) (34), second electron transport layer (second-ETL) (135), electron injection layer (36), and a cathode (110), are deposited in that order; or the layers are deposited the other way around, starting with the cathode (110).

Hereinafter, the embodiments are illustrated in more detail with reference to examples. However, the present disclosure is not limited to the following examples.

In table 2 the comparative compound C-1 is shown, which is used in the comparative example.

In table 3 the inventive compounds Inv-1, Inv-2 and Inv-3 according to formula I are shown, which are used in the examples 1 to 4.

In table 4 prior art compounds are shown, which are used in the device examples.

TABLE 2

| Compound name and IUPAC name | Molecular Structure | Reference |
|---|---|---|
| C-1 7-(3-(anthracen-9-yl)phenyl)dibenzo[c,h]acridine | | US20130200341A1 |

TABLE 3
Inventive compounds Inv-1, Inv-2 and Inv-3 according to formula I used in the examples 1 to 4
| Compound name and IUPAC name | Molecular Structure |
|---|---|
| Inv-1 | 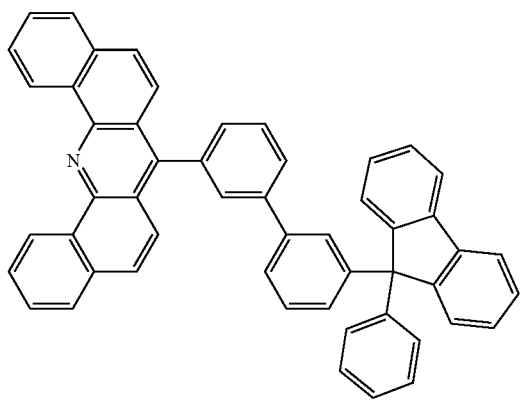 [SMILES: c1ccc(C2(c3cccc(-c4cccc(-c5c6ccc7ccccc7c6nc6c5ccc5ccccc56)c4)c3)c3ccccc3-c3ccccc32)cc1] |
| Inv-2 | 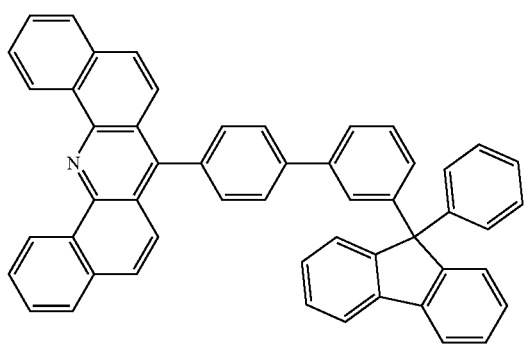 [SMILES: c1ccc(C2(c3cccc(-c4ccc(-c5c6ccc7ccccc7c6nc6c5ccc5ccccc56)cc4)c3)c3ccccc3-c3ccccc32)cc1] |
| Inv-3 | 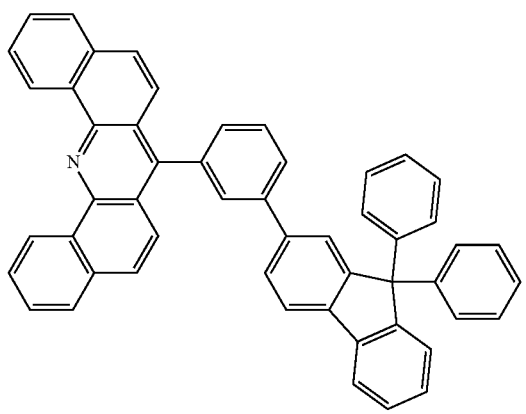 [SMILES: c1ccc(C2(c3ccccc3)c3ccccc3-c3ccc(-c4cccc(-c5c6ccc7ccccc7c6nc6c5ccc5ccccc56)c4)cc32)cc1] |

TABLE 4
| | Prior art compounds used in the examples | |
|---|---|---|
| Compound name and IUPAC name | Molecular Structure | Reference |
| ETM-1 | 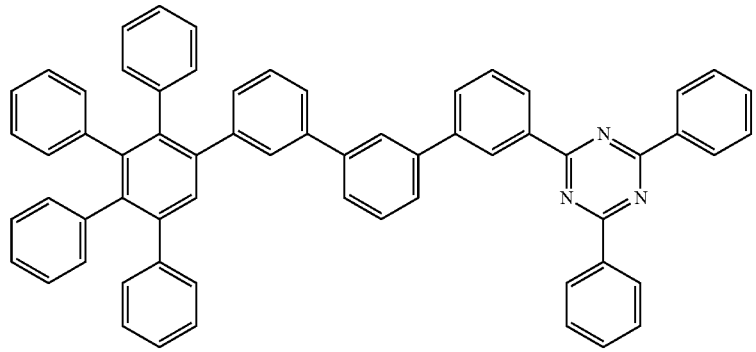 [SMILES: c1ccc(-c2nc(-c3ccccc3)nc(-c3cccc(-c4cccc(-c5cccc(-c6cc(-c7ccccc7)c(-c7ccccc7)c(-c7ccccc7)c6-c6ccccc6)c5)c4)c3)n2)cc1] | WO2016171358 |
| ETM-2 | 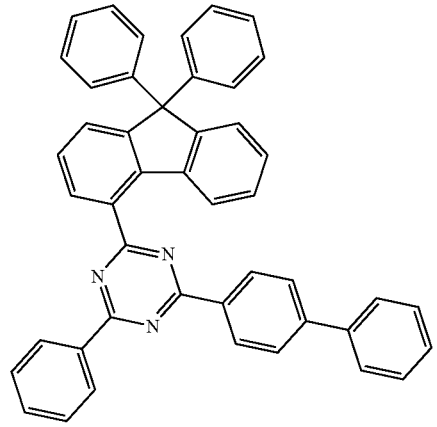 [SMILES: c1ccc(-c2ccc(-c3nc(-c4ccccc4)nc(-c4cccc5c4-c4ccccc4C5(c4ccccc4)c4ccccc4)n3)cc2)cc1] | US2016276596 |
| HTM-1 | 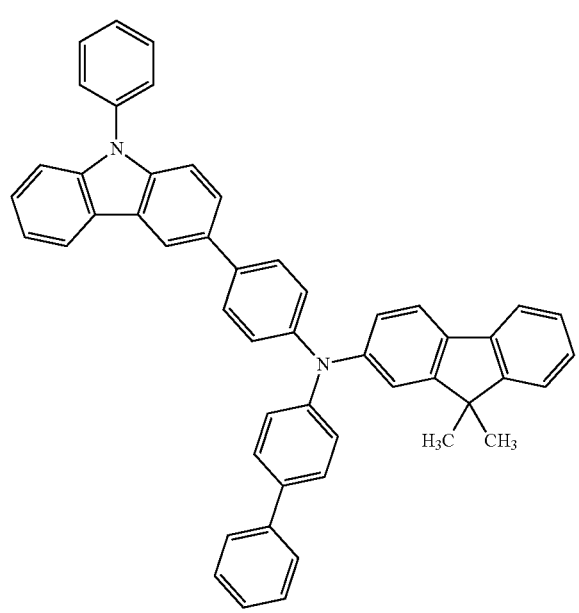 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21] | US2016322581 |

TABLE 4-continued

Prior art compounds used in the examples

| Compound name and IUPAC name | Molecular Structure | Reference |
|---|---|---|
| HTM-2 | 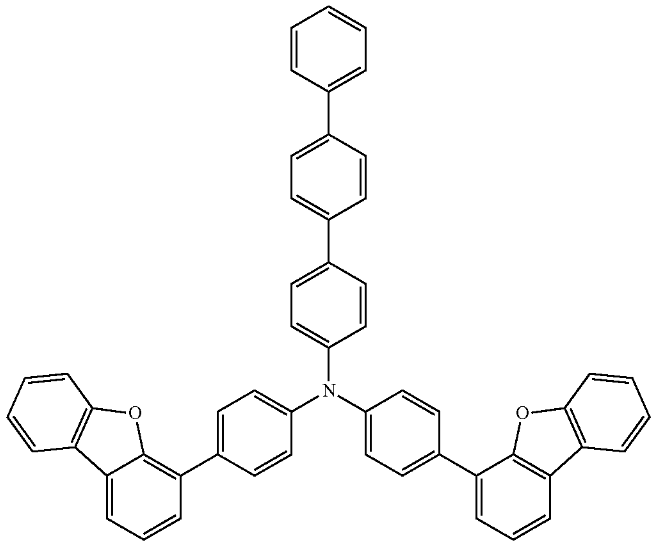 [SMILES: c1ccc(-c2ccc(-c3ccc(N(c4ccc(-c5cccc6c5oc5ccccc56)cc4)c4ccc(-c5cccc6c5oc5ccccc56)cc4)cc3)cc2)cc1] | JP2014096418 A2 |
| DP-1 | 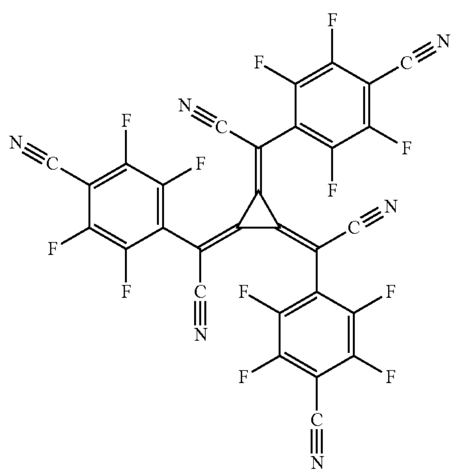 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F] | US2008265216 |
| Host-1 | 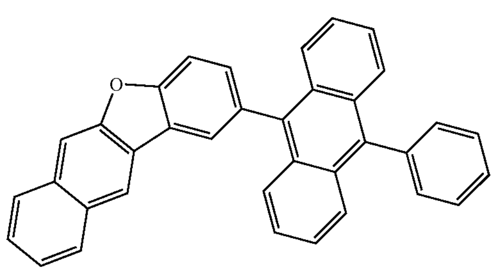 [SMILES: c1ccc(-c2c3ccccc3c(-c3ccc4oc5cc6ccccc6cc5c4c3)c3ccccc23)cc1] | US2015325800 |

TABLE 4-continued

Prior art compounds used in the examples

| Compound name and IUPAC name | Molecular Structure | Reference |
|---|---|---|
| Emitter Dopant NUBD370 from Sun Fine Chem (SFC), Korea | 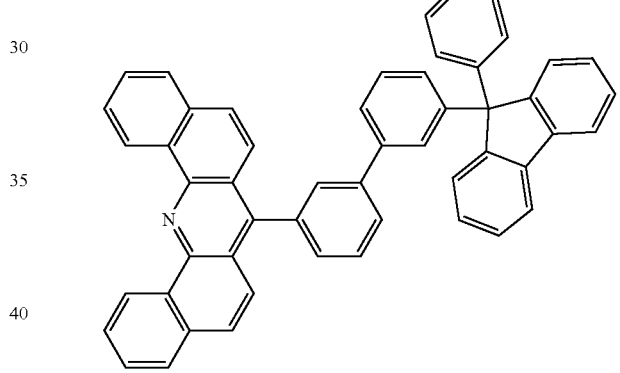 | KR20110015213 |

General Synthesis of Compounds of Formula (I):

Compounds of formula (I), for example Inv-1, Inv-2 and Inv-3, were synthesized by the same coupling reaction. The detailed description is given exemplary for compound Inv-1:

Synthesis of 7-(3'-(9-phenyl-9H-fluoren-9-yl)-[1,1'-biphenyl]-3-yl)dibenzo[c,h]acridine Scheme 1
Synthesis of 7-(3'-(9-phenyl-9H-fluoren-9-yl)-[1,1'-biphenyl]-3-yl) dibenzo [c,h]-acridine.

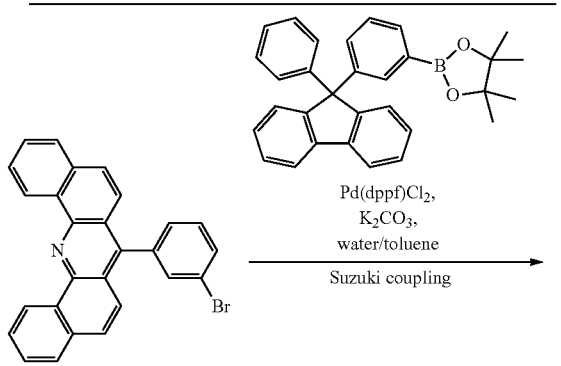

Chemical Formula: C$_{27}$H$_{16}$BrN
Molecular Weight: 434,34

-continued

Chemical Formula: C$_{52}$H$_{33}$N
Molecular Weight: 671,84

Inv-1

A 250-mL-Schenk flask was flushed with nitrogen. In the counterflow of nitrogen, the flask was charged with 7-(3-bromophenyl)dibenzo[c,h]acridine CAS-1352166-95-0 (6.0 g, 13.8 mmol), 4,4,5,5-tetramethyl-2-(3-(9-phenyl-9H-fluoren-9-yl)phenyl)-1,3,2-dioxaborolane CAS-1260032-45-8 (6.73 g, 15.2 mmol), and Pd(dppf)Cl$_2$ (0.20 g, 0.28 mmol). In parallel, an aq. 2 M K$_2$CO$_3$ solution (3.80 g K$_2$CO$_3$, 128.0 mmol in 14 mL H$_2$O) was deaerated by purging with nitrogen for 25 min. In the counterflow of nitrogen, deaerated toluene (85 mL) and the deaerated K$_2$CO$_3$ solution were added to the 250-mL-Schenk flask and the reaction mixture was heated to 100° C. (bath temperature) under a nitrogen atmosphere while stirring. The deep brown suspension showed largely dissolution at reflux temperature. After 22 h, TLC (silica, n-hexane/DCM, 1:1) and HPLC (MSt5186-a, 96.63% product) showed quantitative conversion (R$_t$(7-(3-bromophenyl)dibenzo [c,h]-acridine)=8.4 min).

After a total reaction time of 23 h, the reaction mixture was cooled down to room temperature and the precipitate was isolated by suction filtration over a sintered glass filter and washed with toluene (2×4 mL) and n-hexane (3×6 mL).

The combined filtrates were concentrated to approx. 20 mL using a rotary evaporator and the resulting suspension was stirred for 30 min. at room temperature. The precipitate was isolated by suction filtration over a sintered glass filter and washed with n-hexane (4×6 mL).

After the first filtration step, the yield of the crude product (about 8.8 g, about 92%) was surprisingly low (should be well above 100%), therefore a second crop (2.3 g) was isolated as described above. This can be circumvented by reducing the initial amount of toluene to about 11.8 mL/g 7-(3-bromophenyl)dibenzo[c,h] acridine.

The combined solids (about 11.1 g) were suspended in dichloromethane (about 50 mL) and filtered over a pad of dry Florisil (diameter: 6 cm, height: 4 cm, covered with a filter paper) via suction filtration. Additional dichloromethane (about 650 mL) was used to rinse the product quantitatively. Both filtrates were combined. The combined filtrates were concentrated to an approx. volume of about 150 mL using a rotary evaporator. n-Hexane (about 25 mL) was added and the solvent volume was further reduced to about 50 mL using a rotary evaporator. The obtained suspension was stirred overnight. The solid was collected by suction filtration over a sintered glass filter and washed with n-hexane (3×about 30 mL). After drying at 40° C. under vacuum (about 5 mbar), about 8.22 g (about 88%) of a pale yellow solid were obtained (MSt5186-b, about 99.49%). In order to improve the purity, the solid was dissolved in hot dichloromethane (about 150 mL) and the solution was concentrated to about 100 mL using a rotary evaporator. MTBE (about 70 mL) was added and the solvents were further evaporated using a rotary evaporator to a residual volume of about 50 mL. The obtained suspension was stirred for about 2 h at room temperature. The solid was collected by suction filtration over a sintered glass filter and washed with MTBE (2×about 5 mL). The solid was dried at about 120° C. in vacuo using an oil pump, to afford about 7.5 g (about 11.2 mmol, about 81%) of a pale yellow solid with a purity of about 99.81% according to HPLC (MSt5186-c).

General Procedure for Fabrication of OLEDs

For top emission devices, Examples 1 to 4 and comparative example 1, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes. 100 nm Ag were deposited as anode on the glass at a pressure of $10^{-5}$ to $10^{-7}$ mbar.

OLEDs were prepared to demonstrate the technical benefit utilizing the compounds of formula 1 in an organic electronic device. Table 5 shows the performance parameters of the OLED comprising inventive compounds of formula 1 and the metal complex additive LiQ in a weight ratio of 1:1 in a mixed materials electron transport layer.

In OLED device example 1 an additional undoped electron transport layer was used as a hole-blocking layer.

The layer stack is described by the following text string where the slashes stand for the interface between two adjacent layers: Ag (100 nm)/HTM-1:DP-1 [8 wt %] (10 nm)/HTM-1 (118 nm)/HTM-2 (5 nm)/Host-1:emitter dopant-1 [3 wt %] (20 nm)/ETM-1 (0-5 nm)/Inv1:LiQ or Inv-2:LiQ or Inv-3:LiQ [50 wt %] (31-36 nm)/Yb (2 nm)/Ag (11 nm).

The electron transport layer (second-ETL) 135, if present, is formed with a thickness of 5 nm by depositing ETM-1 on the emission layer 130 according to Example 1, Table 5.

The first electron transport layer 34 is formed either directly on the emission layer 130 according to Comparative Example 1 and Examples 2 to 4 (Table 5), or on the second electron transport layer (second ETL) 135 according to Example 1. If the electron transport layer 34 is in direct contact with the emission layer 130, the thickness is 36 nm. If the electron transport layer 34 is deposited on top of the second electron transport layer (second ETL, second electron transport layer), the thickness is 31 nm.

The electron transport layer comprises 50 wt.-% matrix compound and 50 wt.-% of LiQ.

Then the electron injection layer 36 is formed on top of the first electron transport layer 34 by deposing LiQ with a thickness of 1.5 nm or Yb with a thickness of 2 nm. The cathode was evaporated at ultra-high vacuum of $10^{-7}$ mbar. Therefore, a thermal single co-evaporation of one or several metals was performed with a rate of 0, 1 to 10 nm/s (0.01 to 1 Å/s) in order to generate a homogeneous Ag cathode with a thickness of 11 nm.

A cap layer of Biphenyl-4-yl(9,9-diphenyl-9H-fluoren-2-yl)-[4-(9-phenyl-9H-carbazol-3-yl)phenyl]-amine was formed on the cathode with a thickness of 60 nm in case of MgAg cathode and 75 nm in case of Ag cathode.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured under ambient conditions (20° C.). Current voltage measurements are performed using a Keithley 2400 sourcemeter, and recorded in V. At 10 mA/cm$^2$ for top emission devices, a calibrated spectrometer CAS140 from Instrument Systems is used for measurement of CIE coordinates and brightness in Candela. Lifetime LT of the device is measured at ambient conditions (20° C.) and 10 mA/cm$^2$, using a Keithley 2400 sourcemeter, and recorded in hours.

The brightness of the device is measured using a calibrated photo diode. The lifetime LT is defined as the time till the brightness of the device is reduced to 97% of its initial value.

The light output in external efficiency EQE and power efficiency (1 m/W efficiency) are determined at 10 mA/cm$^2$ for top emission devices.

To determine the efficiency EQE in % the light output of the device is measured using a calibrated photodiode.

To determine the power efficiency in 1 m/W, in a first step the luminance in candela per square meter (cd/m2) is measured with an array spectrometer CAS140 CT from Instrument Systems which has been calibrated by Deutsche Akkreditierungsstelle (DAkkS). In a second step, the luminance is then multiplied by π and divided by the voltage and current density.

In bottom emission devices, the emission is predominately Lambertian and quantified in percent external quantum efficiency (EQE) and power efficiency in 1 m/W.

In top emission devices, the emission is forward directed, non-Lambertian and also highly dependent on the microcavity. Therefore, the external quantum efficiency (EQE) and power efficiency in 1 m/W will be higher compared to bottom emission devices.

Top Emission Devices

In comparative example 1 the OLED comprises a first electron transport layer only and is free of a second electron transport layer. The first electron transport layer (first-ETL) comprises an acridine compound C-1 and alkali organic complex LiQ. The formula of C-1 is

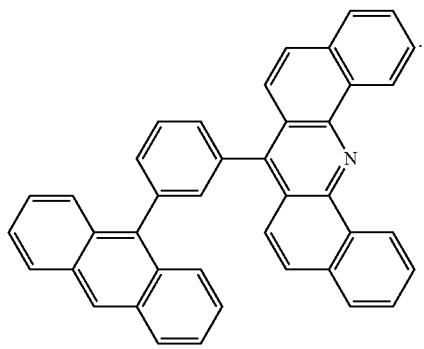

C-1

The glass transition temperature is 121° C. The operating voltage is about 3.20 V, the efficiency is about 7.0 cd/A and the lifetime is about <100 hours.

In examples 1 and 2, the first electron transport layer (first-ETL) comprises a compound of formula I, namely Inv-1 and an alkali organic complex LiQ.

According to example 1 the OLED device comprises in addition a second ETL consisting of compound ETM-1.

Examples 2 to 4 are free of a second electron transport layer (second-ETL). The formula of Inv-1 is:

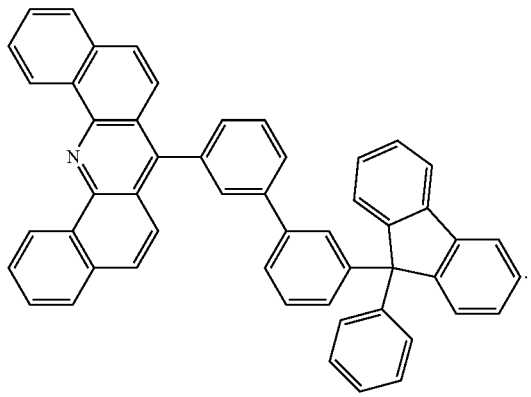

Inv-1

The formula of ETM-1 is:

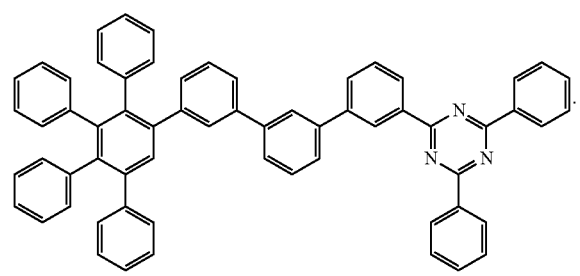

ETM-1

In example 3, the first electron transport layer (first-ETL) comprises a compound of formula I, namely Inv-2 and an alkali organic complex LiQ. Example 3 is free of a second electron transport layer (second-ETL).

The formula of Inv-2 is:

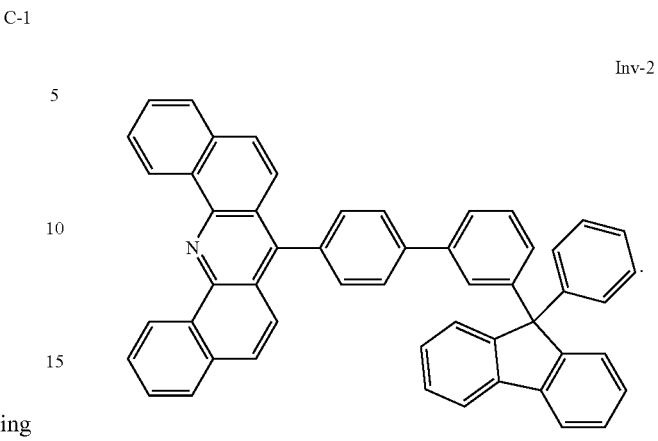

Inv-2

In example 4, the first electron transport layer (first-ETL) comprises a compound of formula I, namely Inv-3 and an alkali organic complex LiQ. Example 4 is free of a second electron transport layer (second-ETL).

The formula of Inv-3 is:

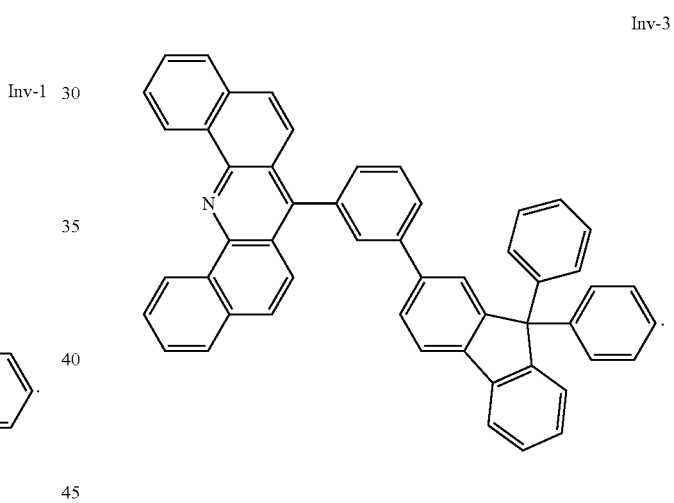

Inv-3

The operating voltage is about 3.42.

In example 5, the first electron transport layer (first-ETL 34) comprises a mixture of the compound ETM-2 and 8-Hydroxyquinolinolato-lithium (LiQ) in a wt % ratio of 1:1. The second electron transport layer (second-ETL 135) comprises the compound Inv-3 of formula (I).

The layer stack of example-5 is described by the following text string where the slashes stand for the interface between two adjacent layers and the layer thickness is given in brackets: Ag (100 nm)/HTM-1:DP-1 [8 wt %] (10 nm) HTM-1 (117 nm)/HTM-2 (5 nm)/Host-1:emitter dopant-1 [3 wt %] (20 nm)/Inv-3 (5 nm)/ETM-2:LiQ [50 wt %] (31 nm)/Yb (2 nm)/Ag (11 nm).

Referring to Tables 5 and 6, the organic light emitting diodes according to Examples 1 to 4 exhibited improved luminance efficiency and/or life-span characteristics simultaneously compared with the organic light emitting diode according to Comparative Example 1. The efficiency is significantly improved for example 1 to 4 in the range of about 7.5 to about 7.8 cd/A and the lifetime is significantly improved in the range of about 150 to about 420 hours.

Table 5 shows the physical data of the OLED device tested for examples 1 to 4 and Comparative example 1.

TABLE 5

| OLED Device | First-ETL | Second-ETL | CIE 1931 y | Voltage at 10 mA/cm² [V] | $C_{Eff}$ at 10 mA/cm² [cd/A] |
|---|---|---|---|---|---|
| Comperative Example 1 | C-1:LiQ | none | 0,047 | 3,2 | 7,0 |
| Example 1 | Inv-1:LiQ | ETM-1 | 0,047 | 3,55 | 7,8 |
| Example 2 | Inv-1:LiQ | none | 0,049 | 3,53 | 7,5 |
| Example 3 | Inv-2:LiQ | none | 0,049 | 3,34 | 7,7 |
| Example 4 | Inv-3:LiQ | none | 0,046 | 3,42 | 7,7 |
| Example 5 | ETM-2*¹:LiQ | Inv-3 | 0.045 | 3,19 | 8.6 |

*¹ = ETM-2 is 2-([1,1'-biphenyl]-4-yl)-4-(9,9-diphenyl-9H-fluoren-4-yl)-6-phenyl-1,3,5-triazine (CAS 1801992-44-8).

Table 6 shows the Tg and life span LT97 of the OLED device tested for examples 2 to 4 and comparative example 1.

Lifetime LT of the device is measured at ambient conditions (20° C.) and 10 mA/cm², using a Keithley 2400 sourcemeter, and recorded in hours. The brightness of the device is measured using a calibrated photo diode. The lifetime LT97 is defined as the time till the brightness of the device is reduced to 97% of its initial value.

TABLE 6

| compound name | Tg [° C.] | LT97 (h) |
|---|---|---|
| C-1 | about 121 | <100 |
| Inv-1 | about 147 | >150 |
| Inv-2 | about 159 | >150 |
| Inv-3 | about 163 | ≥420 |

Table 6 clearly shows that the Tg of inventive compounds according to formula I is significant increased and the life time or life span is significant increased compared to the acridine compound of comparison example C-1.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. An acridine compound of formula (I), with a ring system K1 and K2:

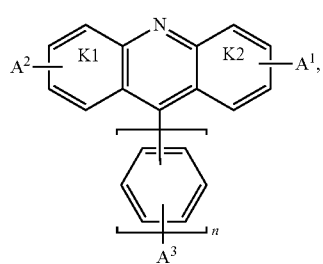

(I)

wherein n is 0, 1 or 2;

$A^1$ and $A^2$ are independently selected from H or aromatic cyclic ring of unsubstituted or substituted phenylene, and the substituents are selected from H, $C_1$ to $C_{18}$ alkyl and $C_1$ to $C_{18}$ alkoxy, and at least one aromatic cyclic ring of $A^1$ and/or $A^2$ are annelated with the ring system K2 or the ring system K1;

$A^3$ has the formula (Ia), having a ring system L1, or has the formula (Ib), having a ring system L2, or has the formula (Ic), or has the formula (Id), or has the formula (Ie), or has the formula (If):

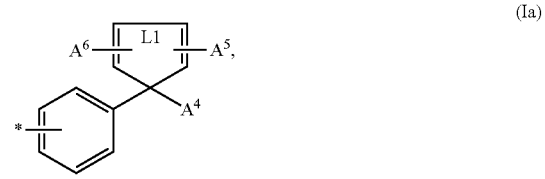
(Ia)

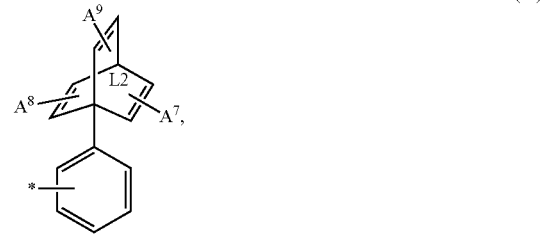
(Ib)

(Ic)

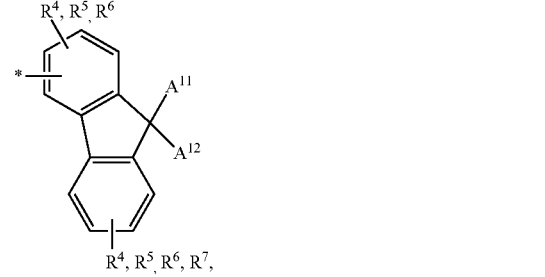
(Id)

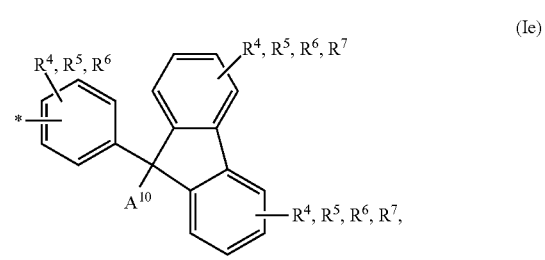
(Ie)

-continued

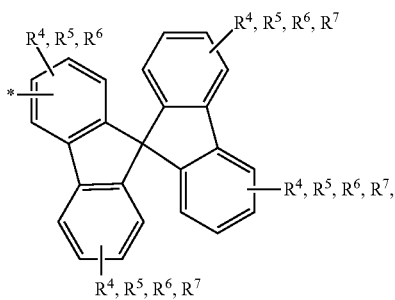

(If)

R¹, R² are independently selected from unsubstituted or substituted $C_6$ to $C_{24}$ aryl and $C_1$ to $C_{18}$ alkyl, and the substituents are independently selected from H, $C_1$ to $C_{18}$ alkyl and $C_1$ to $C_{18}$ alkoxy;

R³ is selected from unsubstituted or substituted $C_6$ to $C_{24}$ aryl, and the substituents are independently selected from H, $C_{18}$ to $C_{18}$ alkyl and $C_1$ to $C_{18}$ alkoxy;

R⁴, R⁵, R⁶ and R⁷ are independently selected from H, unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

A⁴ to A²² are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy;

wherein
at least one of A⁵ and/or A⁶ are annelated with the ring system L1;
wherein
at least one of A⁷ and/or A⁸ and/or A⁹ annelated with the ring system L2;
wherein
formulas (Ia) to (If) of A³ are connected at the position marked with "*" via a single bond; and
wherein when A³ has the formula (Id)—
(i) n is 1 or 2,
(ii) R⁴, R⁵, R⁶ and R⁷ are independently selected from H and unsubstituted $C_6$ to $C_{18}$ aryl, or
(iii) n is 1 or 2, and R⁴, R⁵, R⁶ and R⁷ are independently selected from H and unsubstituted $C_6$ to $C_{18}$ aryl.

2. The acridine compound according to claim 1, wherein for formula (I):
n is 0, 1 or 2;
A¹ and A² are independently selected from H and or aromatic cyclic ring of unsubstituted or substituted phenylene, and the phenylene of A¹ and/or A² are annelated with the ring system K2 or the ring system K1,
A³ has the formula selected from Ia, Ib, Ic, Id, Ie or If, wherein for formula (Ia):
A⁴, A⁵ and A⁶ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula (Ib):
A⁷, A⁸ and A⁹ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;

wherein for formula (Ic):
R¹, R² are independently selected from unsubstituted or substituted $C_6$ to $C_{18}$ aryl and $C_1$ to $C_{18}$ alkyl, and the substituents are independently selected from H, $C_1$ to $C_{12}$ alkyl and $C_1$ to $C_{12}$ alkoxy;
R³ is selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula (Id), (Ie) and (If):
R⁴, R⁵, R⁶ and R⁷ are independently selected from H, unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy, and
A¹⁰, A¹¹, A¹² are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy; and
wherein
for the substituent Id: n=1 or 2.

3. The acridine compound according to claim 1, wherein for formula (I):
R⁴, R⁵, R⁶ and R⁷ are independently selected from H, unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy,
wherein for the substituents R⁴, R⁵, R⁶ and R⁷ pyridyl is excluded if n=0.

4. The acridine compound according to claim 1, wherein n is 0 or 1;
A¹ and A² are independently selected from H and phenylene;
A³ has the formula selected from (Ia) to (If);
wherein for formula (Ia):
A⁴, A⁵ and A⁶ are independently selected from unsubstituted $C_6$ to $C_{18}$ aryl;
wherein for formula (Ib):
A⁷, A⁸ and A⁹ are independently selected from unsubstituted $C_6$ to $C_{18}$ aryl;
wherein for formula (Ic):
R¹, R² are independently selected from unsubstituted $C_6$ to $C_{18}$ aryl and $C_1$ to $C_{18}$ alkyl;
R³ is selected from unsubstituted $C_6$ to $C_{18}$ aryl;
wherein for formula (Id), (Ie) and (If):
R⁴, R⁵, R⁶ and R⁷ are independently selected from H, unsubstituted $C_6$ to $C_{18}$ aryl;
A¹⁰, A¹¹ and A¹² are independently selected from unsubstituted $C_6$ to $C_{18}$ aryl.

5. The acridine compound according claim 1, wherein the acridine compound is selected from formula (F1) to (F5):

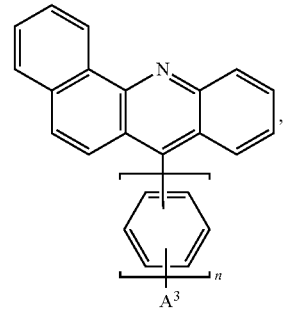

(F1)

(F2) 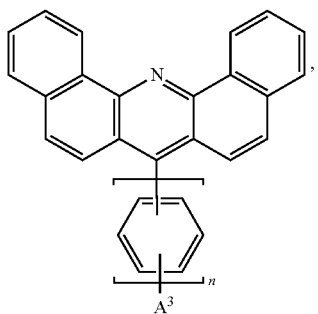
(F3) 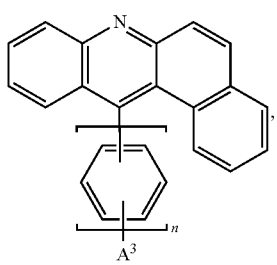
(F4) 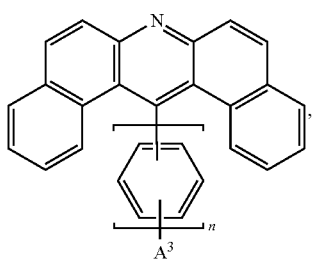
(F5) 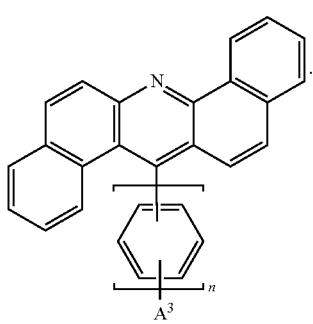
6. The acridine compound according to claim 1, wherein the acridine compound is selected from formula (D1) to (D16):
(D1) 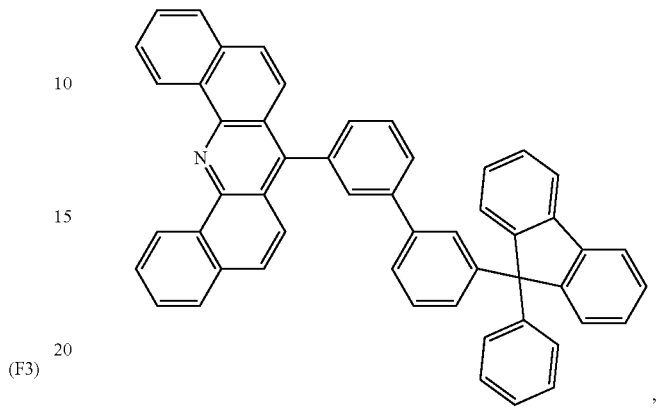
(D2) 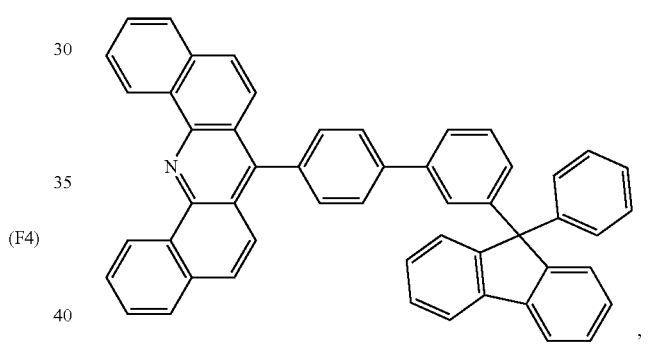
(D3) 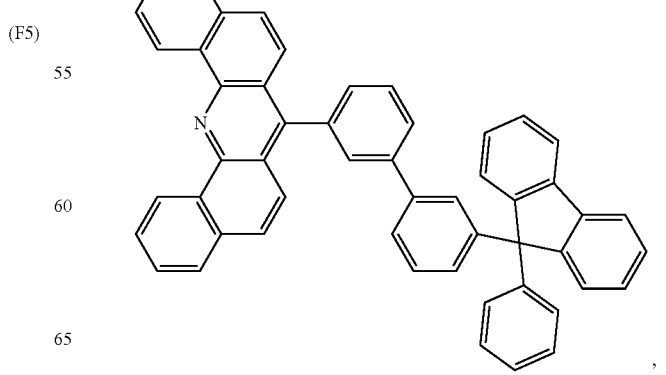

(D4)
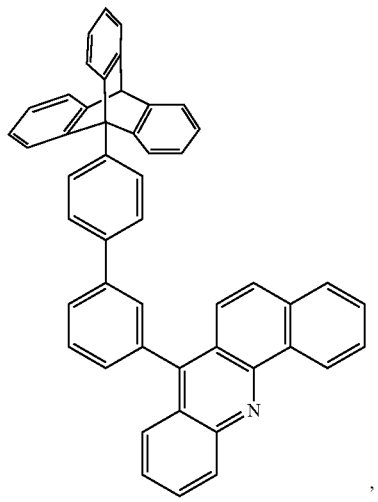
(D5)
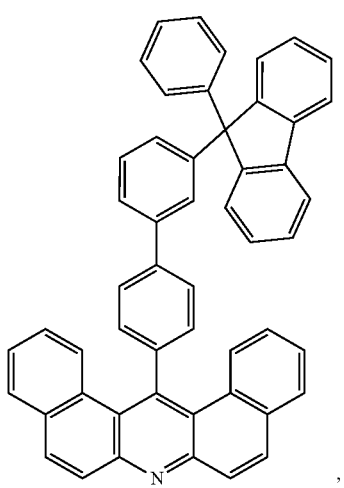
(D6)
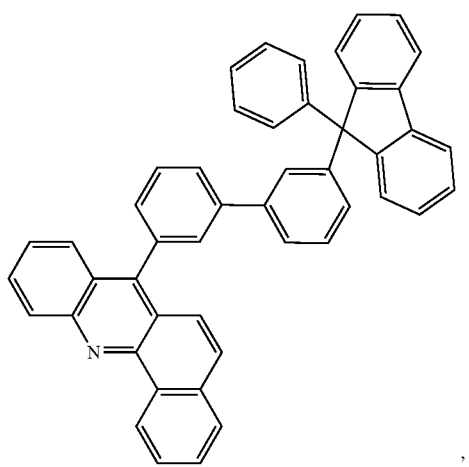
(D7)
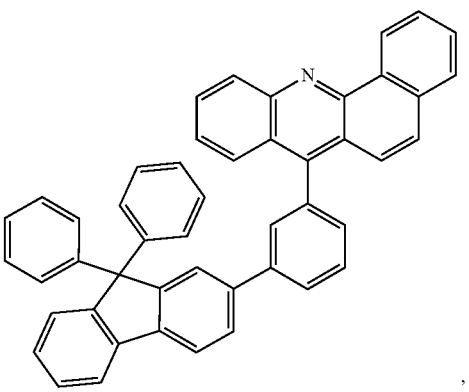
(D8)
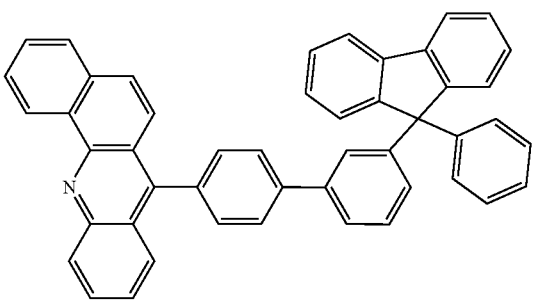
,
(D9)
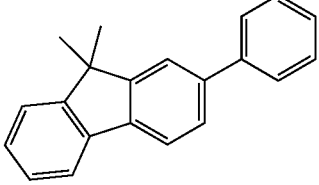
,
(D10)
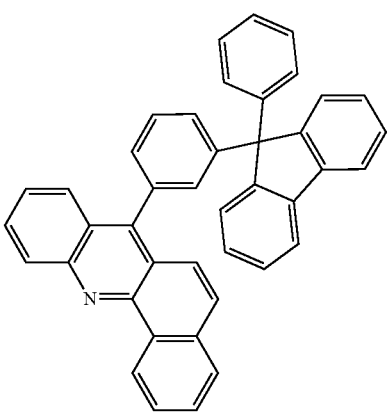
, (D11) 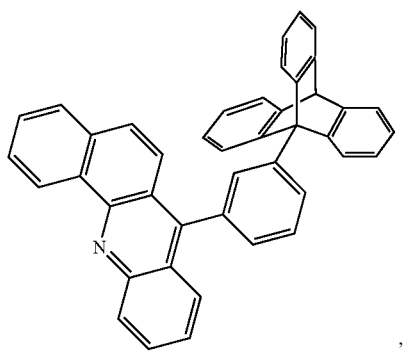

(D12) 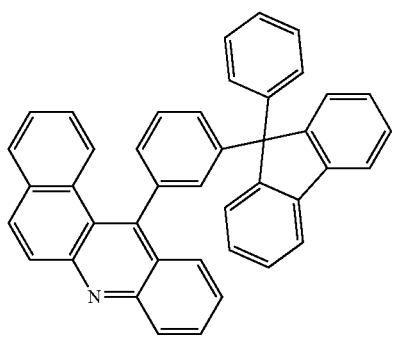

(D13) 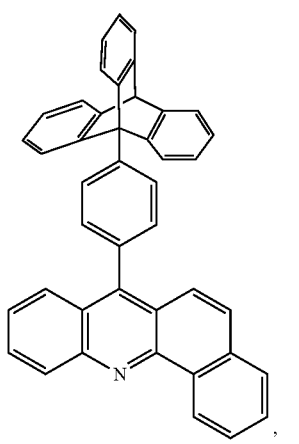

(D14) 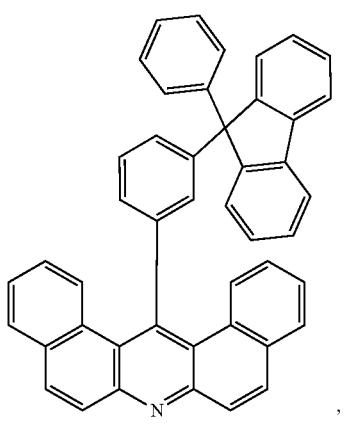

(D15) 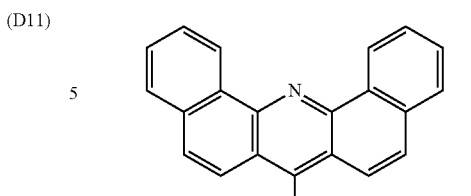

(D16) 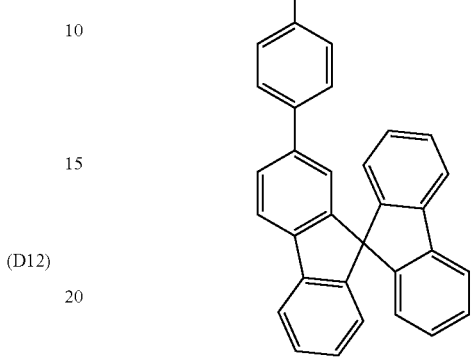

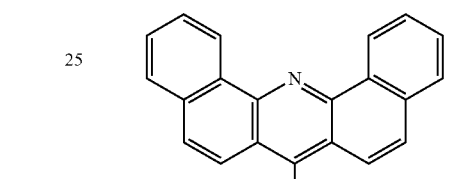

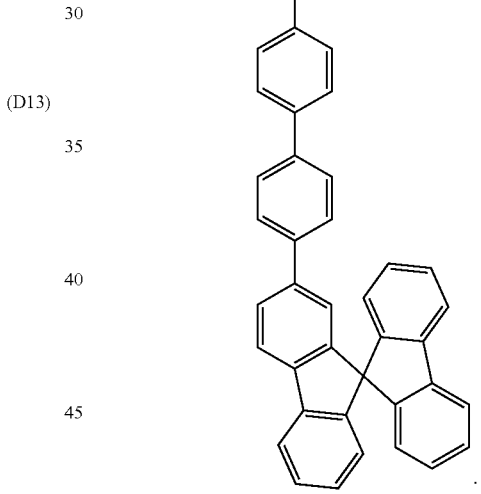

7. A semiconductor layer, wherein the semiconductor layer comprises or consists of at least one compound of formula (I) according to claim 1.

8. The semiconductor layer according to claim 7, wherein the semiconductor layer is an electron transport layer.

9. The semiconductor layer according to claim 7, wherein the semiconductor layer further comprises at least one alkali halide or alkali organic complex.

10. An electronic device comprising at least one semiconductor layer according to claim 7.

11. The electronic device according to claim 10, wherein the at least one semiconductor layer further comprises at least one alkali halide or alkali organic organic complex.

12. The electronic device according to claim 10, wherein the electronic device comprises at least one semiconductor layer that is a first electron transport layer.

13. The electronic device according to according to claim 10, further comprising at least one anode layer, at least one cathode layer and at least one emission layer.

14. The electronic device according to according to claim 10, wherein the electronic device is a light emitting device, a light emitting diode, thin film transistor, a battery or a photovoltaic cell.

15. The electronic device according to claim 10, wherein the electronic device is a display device.

16. The semiconductor layer according to claim 7, wherein for formula (I):
n is 0, 1 or 2;
$A^1$ and $A^2$ are independently selected from H and or aromatic cyclic ring of unsubstituted or substituted phenylene, and the phenylene of $A^1$ and/or $A^2$ are annelated with the ring system K2 or the ring system K1,
$A^3$ has the formula selected from Ia, Ib, Ic, Id, Ie or If, wherein for formula (Ia):
$A^4$, $A^5$ and $A^6$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula (Ib):
$A^7$, $A^8$ and $A^9$ are independently selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula (Ic):
$R^1$, $R^2$ are independently selected from unsubstituted or substituted $C_6$ to $C_{18}$ aryl and $C_1$ to $C_{18}$ alkyl, and the substituents are independently selected from H, $C_1$ to $C_{12}$ alkyl and $C_1$ to $C_{12}$ alkoxy;
$R^3$ is selected from unsubstituted or substituted $C_6$ to $C_{18}$ aryl, and the substituents are independently selected from H, $C_1$ to $C_{12}$ alkyl and $C_1$ to $C_{12}$ alkoxy;
wherein for formula (Id), (Ie) and (If):
$R^4$, $R^5$, $R^6$ and $R^7$ are independently selected from H, unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy, and
$A^{10}$, $A^{11}$, $A^{12}$ are independently selected from unsubstituted or substituted $C_6$ to $C_{24}$ aryl and unsubstituted or substituted pyridyl, and the substituents are independently selected from H, $C_1$ to $C_{18}$ alkyl and $C_1$ to $C_{18}$ alkoxy; and
wherein
for the substituent Id: n=1 or 2.

17. The semiconductor layer according to claim 7, wherein for formula (I):
$R^4$, $R^5$, $R^6$ and $R^7$ are independently selected from H, unsubstituted or substituted $C_6$ to $C_{18}$ aryl and unsubstituted or substituted pyridyl, and the substituents are independently selected from H, $C_1$ to $C_{12}$ alkyl and $C_1$ to $C_{12}$ alkoxy,
wherein for the substituents $R^4$, $R^5$, $R^6$ and $R^7$ pyridyl is excluded if n=0.

18. The semiconductor layer according to claim 7, wherein
n is 0 or 1;
$A^1$ and $A^2$ are independently selected from H and phenylene;
$A^3$ has the formula selected from (Ia) to (If);
wherein for formula (Ia):
$A^4$, $A^5$ and $A^6$ are independently selected from unsubstituted $C_6$ to $C_{18}$ aryl;

wherein for formula (Ib):
$A^7$, $A^8$ and $A^9$ are independently selected from unsubstituted $C_6$ to $C_{18}$ aryl;
wherein for formula (Ic):
$R^1$, $R^2$ are independently selected from unsubstituted $C_6$ to $C_{18}$ aryl and $C^1$ to $C^{18}$ alkyl;
$R^3$ is selected from unsubstituted $C_6$ to $C_{18}$ aryl;
wherein for formula (Id), (Ie) and (If):
$R^4$, $R^5$, $R^6$ and $R^7$ are independently selected from H, unsubstituted $C_6$ to $C_{18}$ aryl;
$A^{10}$, $A^{11}$, and $A^{12}$ are independently selected from unsubstituted $C_6$ to $C_{18}$ aryl.

19. The semiconductor layer according to claim 7, wherein the acridine compound is selected from formula (F1) to (F5):

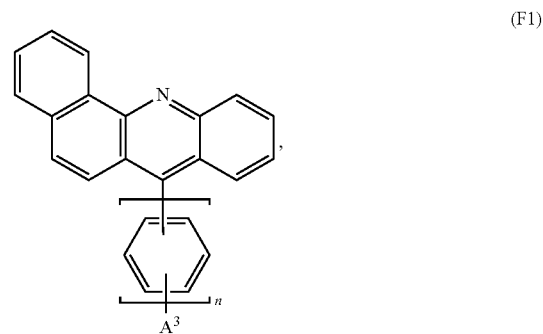

(F1)

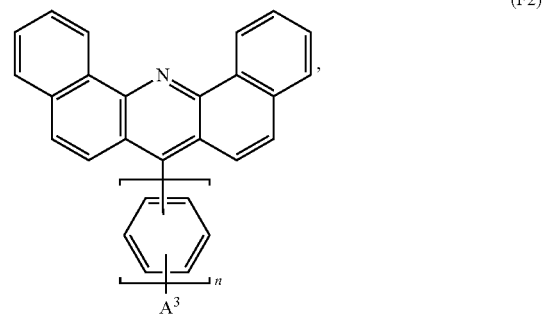

(F2)

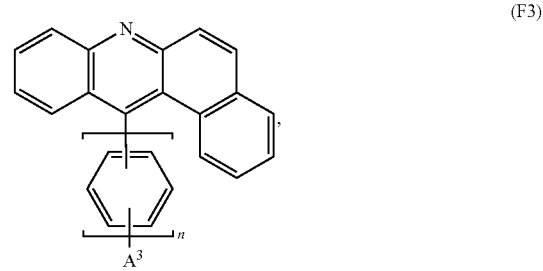

(F3)

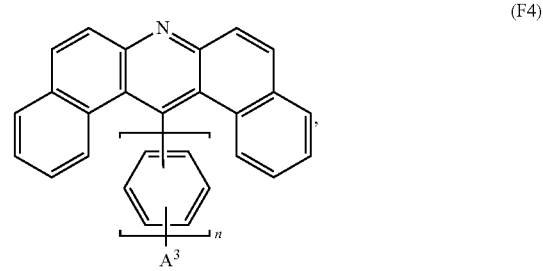

(F4)

(F5)
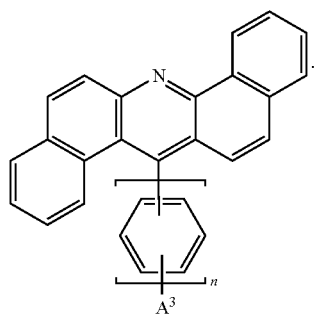
20. The semiconductor layer according to claim 7, wherein the acridine compound is selected from formula (D1) to (D16):
(D1)
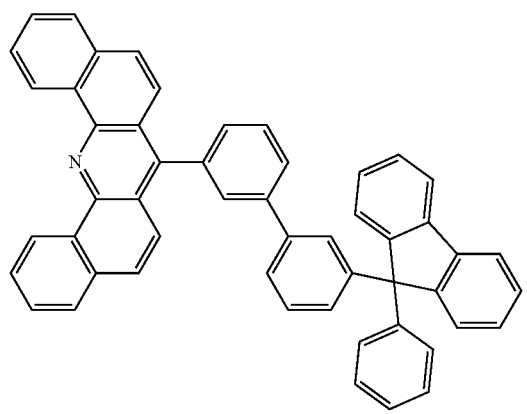
,
(D2)
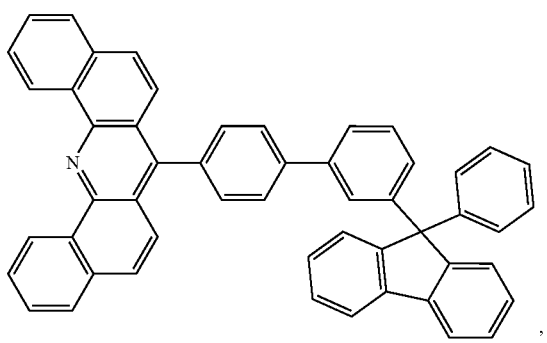
,
(D3)
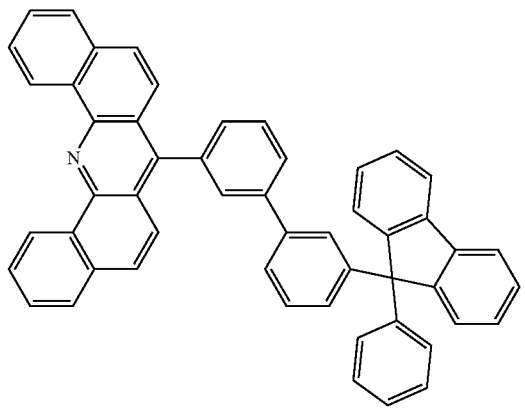
,
(D4)
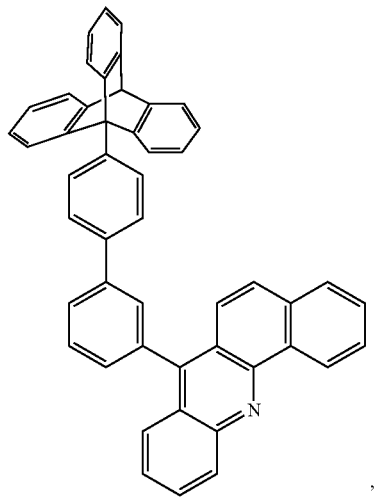
,
(D5)
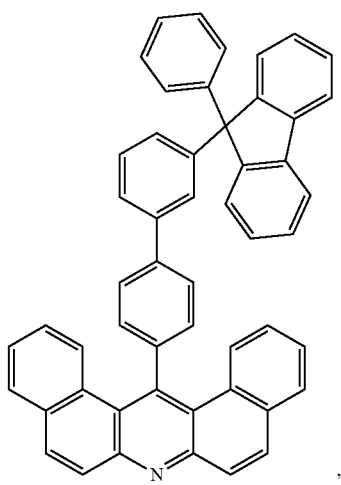
, (D6)
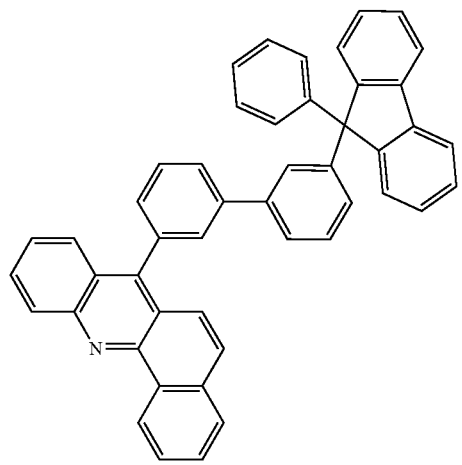
(D7)
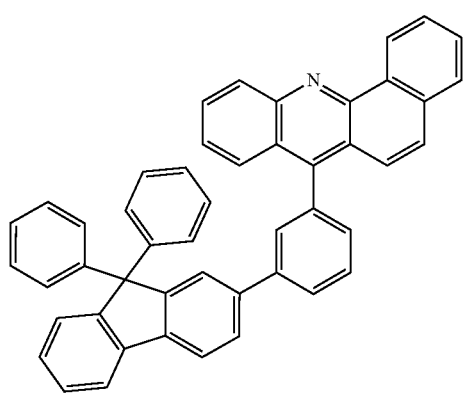
(D8)
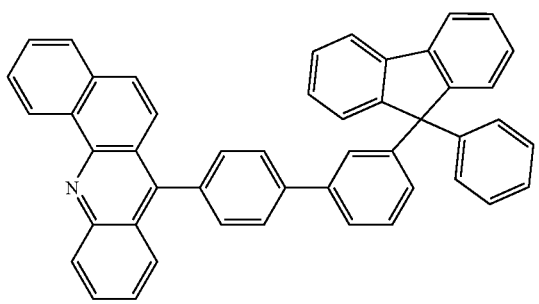
(D9)
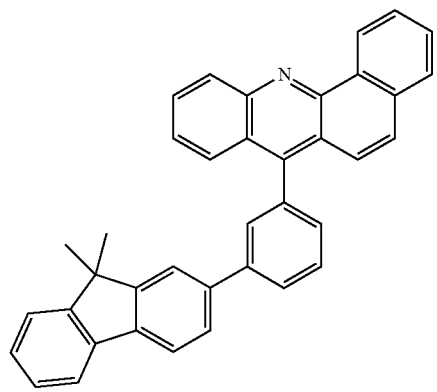
(D10)
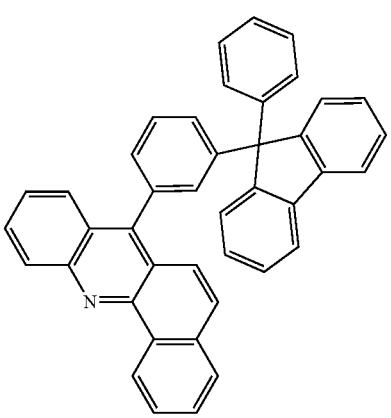
(D11)
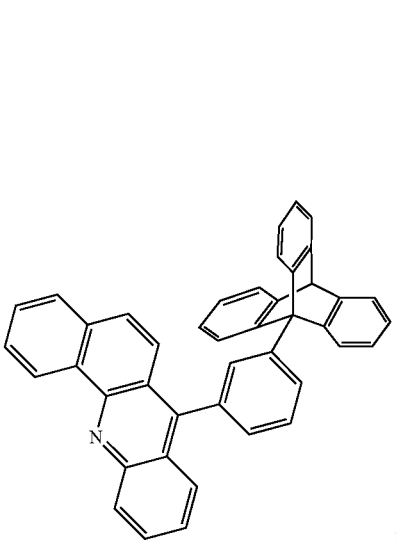
(D12)
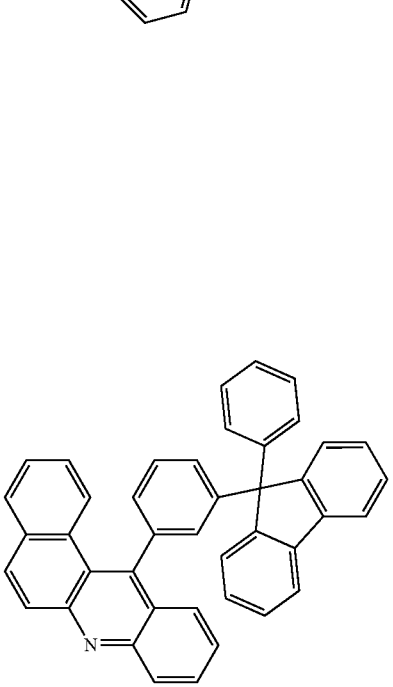

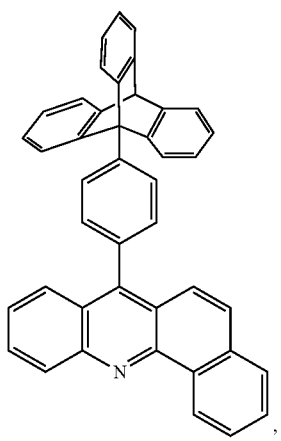
(D13)
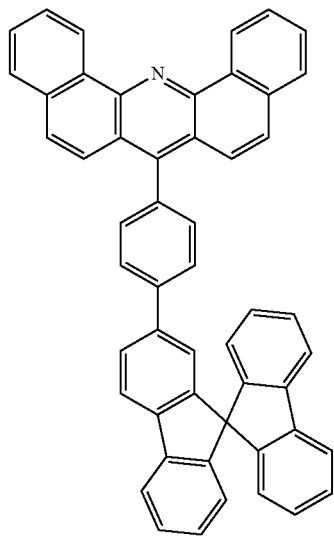
(D15)
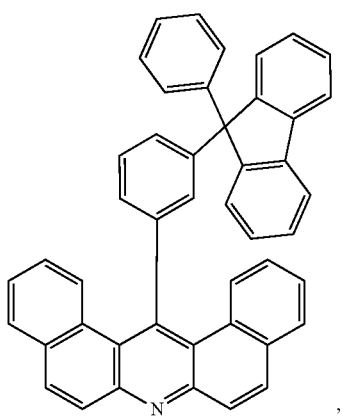
(D14)
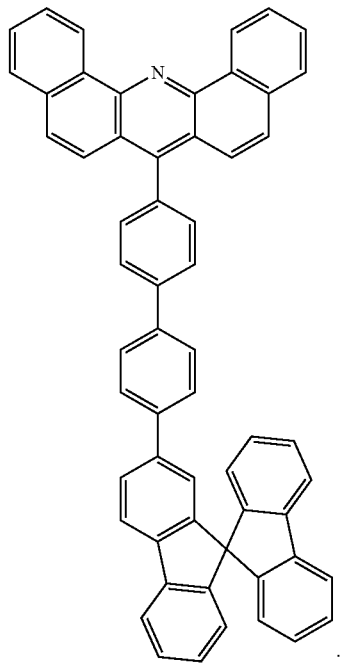
(D16)
* * * * *